(12) United States Patent
Hladky et al.

(10) Patent No.: US 7,265,559 B1
(45) Date of Patent: *Sep. 4, 2007

(54) SELF-CALIBRATING CORROSION MEASUREMENT FIELD DEVICE WITH IMPROVED SIGNAL MEASUREMENT AND EXCITATION CIRCUITRY

(75) Inventors: Karel Hladky, Manchester (GB); Denis M. Poirier, Cleveland Heights, OH (US)

(73) Assignee: Pepperl + Fuchs, Twinsburg, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/457,155

(22) Filed: Jul. 13, 2006

(51) Int. Cl.
G01R 27/08 (2006.01)
G01N 22/26 (2006.01)

(52) U.S. Cl. ............... 324/700; 204/404; 205/775.5

(58) Field of Classification Search .............. 324/700
See application file for complete search history.

(56) References Cited

U.S. PATENT DOCUMENTS

| | | | |
|---|---|---|---|
| 4,238,298 A | 12/1980 | Tsuru et al. | |
| 4,395,318 A | 7/1983 | Tait et al. | |
| 4,488,939 A | 12/1984 | Fu | |
| 4,564,422 A | 1/1986 | Simoneau et al. | |
| 4,575,678 A | 3/1986 | Hladky | |
| 5,006,786 A | 4/1991 | McKubre et al. | |
| 5,139,627 A | 8/1992 | Eden et al. | |
| 5,151,163 A | 9/1992 | Miller | |
| 5,286,357 A | 2/1994 | Smart et al. | |
| 5,323,429 A | 6/1994 | Roarty et al. | |
| 5,425,867 A | 6/1995 | Dawson et al. | |
| 5,519,330 A | 5/1996 | Yamauchi et al. | |
| 5,792,337 A | 8/1998 | Padovani et al. | |
| 5,854,557 A | 12/1998 | Tiefnig | |
| 5,858,204 A | 1/1999 | Jambo et al. | |
| 5,888,374 A | 3/1999 | Pope et al. | |
| 6,010,889 A | 1/2000 | Gearey et al. | |
| 6,015,484 A | 1/2000 | Martinchek et al. | |
| 6,079,276 A * | 6/2000 | Frick et al. | 73/718 |
| 6,132,593 A | 10/2000 | Tan | |
| 6,264,824 B1 | 7/2001 | Reid et al. | |
| 6,425,290 B2 | 7/2002 | Willcox et al. | |
| 6,690,182 B2 | 2/2004 | Kelly et al. | |
| 6,919,729 B2 | 7/2005 | Tiefnig | |
| 6,946,855 B1 | 9/2005 | Hemblade | |
| 2005/0011278 A1 | 1/2005 | Brown et al. | |
| 2005/0122121 A1 | 6/2005 | Gilboe | |
| 2005/0212534 A1 | 9/2005 | Cottis | |
| 2006/0125493 A1 | 6/2006 | Subramanian et al. | |
| 2006/0144719 A1 | 7/2006 | Gill et al. | |

* cited by examiner

*Primary Examiner*—Vincent Q. Nguyen
(74) *Attorney, Agent, or Firm*—Fay Sharpe LLP

(57) ABSTRACT

Low power corrosion measurement devices are described with improved signal measurement and excitation circuitry in a field transmitter for online corrosion monitoring or off-line corrosion data logging.

19 Claims, 11 Drawing Sheets

| Measurement | U13 | U14 | U15 | U16 |
|---|---|---|---|---|
| SRM (Rs) | OSC. | 1 | OSC. | 0 |
| HDA | 0 | 1 | 0 | 0 |
| LPR | 0 | 1 | 0 | 0 |
| Cell Offset V | X | X | X | 1 |
| ECN | 0 | 0 | 0 | 0 |
FIG. 4
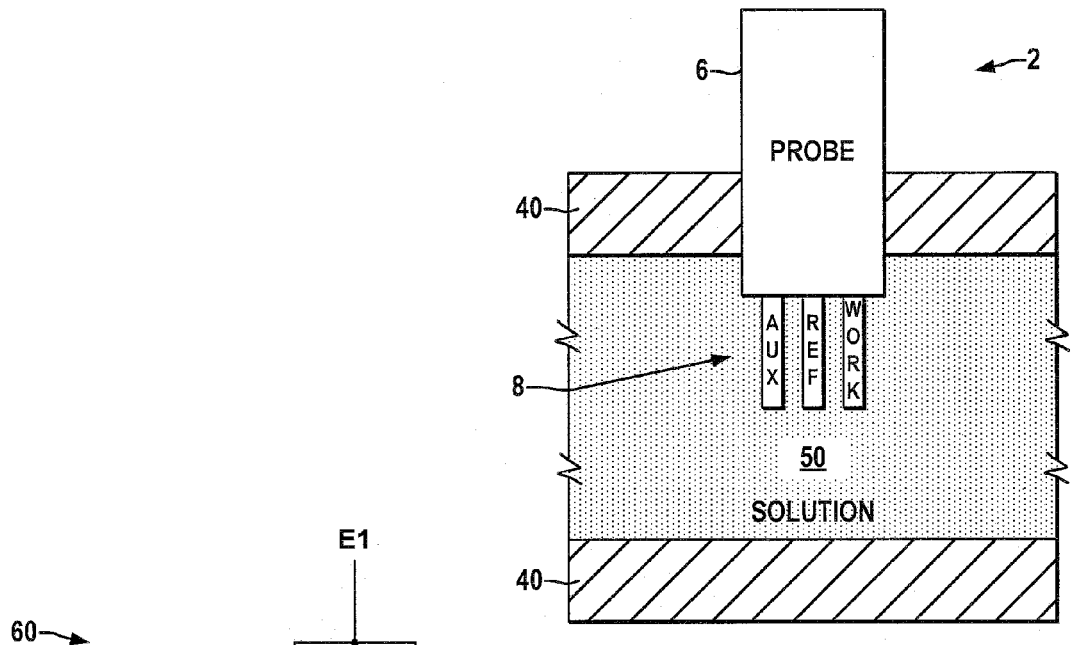
FIG. 5
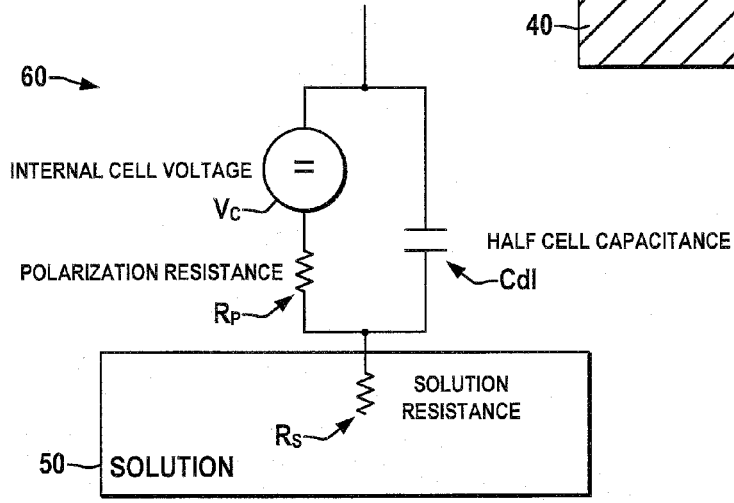
FIG. 6

SELF-CALIBRATING CORROSION MEASUREMENT FIELD DEVICE WITH IMPROVED SIGNAL MEASUREMENT AND EXCITATION CIRCUITRY

FIELD OF THE INVENTION

The present invention relates generally to corrosion measurement and more particularly to low power field devices for measuring corrosion.

BACKGROUND OF THE INVENTION

Field installed transmitter devices have been widely employed in process control situations to provide process variable information to control and/or data acquisition devices. Unlike laboratory measurement instrumentation, field devices are constructed using sealed protective enclosures to withstand adverse environmental conditions in manufacturing facilities, chemical processing plants, oil refineries and the like, in which the device may be subjected to extreme temperatures and humidity. Such devices are typically employed in distributed control systems for sensing temperature, fluid pressure, flow, and other variables used to control an ongoing process and are generally connected to other control equipment by a 4-20 mA control loop from which the transmitter derives its power and through which the sensed process variable is provided to the control system. Loop-powered transmitters are widely available for sensing various process variables, with the transmitter generally being configured to vary the loop current from 4 mA to 20 mA according to the measured process variable (e.g., with 0% of the process variable range being represented by 4 mA and 100% corresponding to 20 mA). Other transmitters offer digital communications according to standard protocols such as HART, etc. by which the transmitter can send and receive data, commands, and other information via the control loop.

Many chemical processes involve storage or transport of fluids in or through pipes, tanks and other structures, wherein these structures may corrode overtime due to contact with the transported or stored fluids. In these situations, it is desirable to ascertain the amount and rate of such corrosion to allow informed evaluation of the structural integrity for maintenance purposes and also to identify undesired or unexpected corrosivity levels in the fluids themselves, where the corrosion data may be used to apply remedial measures such as inhibitor injection and/or to ascertain and optimize the efficiency of such remedial measures. Other corrosion measurement applications include corrosion of structures exposed to non-fluids, such as corrosion of steel in concrete, wherein corrosion-causing materials generally, whether solid, liquid, or gaseous are referred to as electrolytes. However, it is often impractical to perform corrosion measurement using elaborate and expensive laboratory grade instrumentation and measurement systems due to the nature of most chemical processing environments and the size and location of pipelines and fluid holding tanks. In particular, such expensive systems are not adaptable to online measurement of pipeline or storage tank corrosion conditions in real time. Moreover, online measurement devices must be able to operate on very low power budgets, such as obtainable from a standard 4-20 mA control loop or from battery power. Field corrosion transmitters have recently been introduced to provide corrosion measurement capabilities for these applications. However, conventional field corrosion transmitters have thusfar been unable to provide requisite levels of corrosion measurement accuracy and adaptability to measuring corrosion with respect to a wide variety of structure materials, transported fluid types, and temperatures whereby a need exists for improved field transmitters for measuring one or more corrosion related values.

SUMMARY OF INVENTION

Various aspects of the present invention are now summarized to facilitate a basic understanding of the invention, wherein this summary is not an extensive overview of the invention, and is intended neither to identify certain elements of the invention, nor to delineate the scope thereof. Instead, the primary purpose of this summary is to present some concepts of the invention in a simplified form prior to the more detailed description that is presented hereinafter. The invention relates to low power field devices for accurately measuring one or more corrosion related values such as corrosion rate, localized corrosion (e.g., pitting), solution (electrolyte) resistance or conductivity, etc. in real time, and which can be employed in field situations not amenable to expensive and delicate laboratory instrumentation systems.

In accordance with one or more aspects of the invention, loop-powered corrosion measurement devices are provided for measuring or monitoring corrosion of a structure exposed to an electrolyte. The devices comprise a power system to power the device using power from a 4-20 mA loop, battery, solar panel, etc. and a probe interface system with signal conditioning circuitry to interface with two or more measurement electrodes situated in the electrolyte. The signal conditioning provides one or more excitation signals to the electrolyte via a first electrode and includes sensing circuitry for sensing one or more corrosion-related electrical signals such as currents, voltages, etc. via at least a second one of the electrodes. In certain embodiments, a switching system is provided with a plurality of analog switches operable according to corresponding control signals to selectively interconnect circuit components of the excitation and sensing circuitry and the electrodes in a plurality of different configurations to facilitate providing corrosion related values such as electrolyte resistance or conductivity, corrosion rate, localized corrosion index, etc., using one or more measurement types including but not limited to solution (electrolyte) resistance (conductivity) measurement (SRM), harmonic distortion analysis (HDA), linear polarization resistance measurement (LPR), electrochemical noise measurement (ECN), etc. The switching system may also operate to couple a driver amplifier of the excitation circuitry such that the excitation (auxiliary) and sensing (working) electrodes are in a feedback path of the driver amplifier, by which current flowing between these electrodes causes the voltage between the working electrode and a reference electrode to be the same as the applied excitation voltage. In certain embodiments, moreover, the switching system connects a current limiting resistor of the sensing circuitry in a feedback path of a current to voltage converter circuit, so that the current limiting resistance does not influence the current sensing operation.

The devices also include a processing system, for example, including a microprocessor, microcontroller, DSP, etc., operatively coupled with the probe interface to control the excitation signals provided to the electrolyte, to selectively configure and operate the sensing components, and to compute one or more corrosion related values based on measured values from the sensing circuitry. The processor also operates to store computed corrosion values in non-volatile memory for subsequent uploading. The corrosion value(s) may be provided as a process variable output in the form of a 4-20 mA signal on a connected control loop. The device may also include a communications interface for HART or other type digital communications allowing user configuration of the number of measurements and measurement types in a given device cycle, and for providing the user with corrosion related values via the loop or other wired or wireless communications.

In accordance with other aspects of the invention, a rectifier system is coupled with the sensing circuitry to provide a non-dc-free signal to an analog-to-digital (A/D) converter based on a dc-free sensed signal, which may be part of a synchronous rectifier that alternates a polarity of a sensed signal in concert with an alternating polarity of an excitation signal provided to the electrolyte. In this manner, the A/D input has a non-zero average value allowing sub-Nyquist sampling rates and averaging to ascertain the value of the measured current. The use of the rectifier facilitates the provision of substantially dc-free square wave excitation signals to mitigate inaccuracies and corrosion exacerbation associated with non-dc-free signals, while also facilitating conservation of device power so that the processing system can average a number of sensed current readings taken at low A/D sampling rates in measuring electrolyte resistance/conductivity. In one example, the synchronous rectifier is comprised of a first switch toggled by the processor to alternate the polarity of a sensed signal and a second switch that synchronously alternates the polarity of the excitation signal to provide an essentially dc-free AC excitation signal to the electrolyte at an excitation frequency with the analog-to-digital converter receiving a non-dc-free signal which can be sampled at a much lower sampling rate and averaged to measure the electrolyte resistance accurately. In one embodiment, the dc-free square wave excitation is provided at a frequency of about 500 Hz or less, preferably about 100-200 Hz, with the A/D converter sampling the sensed current at a rate of less than about ten samples per second.

In accordance with further aspects of the invention, the device includes an isolation barrier providing galvanic isolation of the electrodes from the 4-20 mA loop, by which the device is easily incorporated in a given plant installation without the need for a separate isolation barrier. Other aspects of the invention involve providing intrinsic safety circuitry in the device to protect against high currents and/or high voltages, which may be a two-stage system, and which may include resistors for protecting the electrodes.

According to still further aspects of the invention, the device can operate as a stand-alone data acquisition and storage device, where the processor computes corrosion related values in each of a series of device cycles and stores the computed corrosion related values for subsequent retrieval by a user, where the values may be stored in non-volatile memory in the device. In this aspect, the device may interface with an external communications device through a control loop or other wired or wireless means to allow a user to configure the device and/or to retrieve stored computed corrosion related values therefrom using HART or other suitable communications protocol(s) wherein the device may store one or more day's worth of computed corrosion related values.

In accordance with further aspects of the invention, the electrolyte resistance measurement may be improved by dynamically adjusting the AC excitation amplitude to better utilize the input range of the A/D converter, wherein the processing system provides the excitation signal at a first amplitude and selectively increases the excitation signal amplitude until a resulting sensed current signal exceeds a predefined threshold value.

According to still further aspects of the invention, the device is operative to self-calibrate in order to compensate for offset errors in the current sensing and rectifier circuitry, wherein the processing system controls the excitation circuit to initially provide no excitation signal and causes the synchronous rectifier to begin alternating the polarity of a sensed current signal. The processor samples the sensed current using the A/D converter while the synchronous rectifier operates with no excitation signal, and computes an offset value based on one or more sensed current signal samples. The computed offset value is then stored for subsequent use as an offset correction in computing the electrolyte resistance or other corrosion related values.

In another aspect, the excitation is adjusted during HDA measurements to compensate for differences in the electrodes, wherein the processing system measures a sensed voltage signal with no applied excitation signal, stores the sensed voltage value as an offset, and thereafter causes the excitation circuitry to provide sinusoidal excitation voltage signals with the offset and computes the corrosion related value(s) using HDA based on harmonics of sensed current signals.

In accordance with other aspects of the invention, improved harmonic distortion analysis (HDA) type measurements are facilitated using sinusoidal AC excitation at a frequency of about 50 mHz or more, wherein the device computes one or more corrosion related values based on more than one cycle (preferably about 10 to 20 cycles) of the sensed sinusoidal current signal. This facilitates the measurement of corrosion rate using enough current samples to adequately perform Fourier analysis for obtaining current harmonic readings without significantly lengthening the device measurement cycle time.

Still further aspects of the invention relate to dynamic algorithm changes in which HDA measurements and computations are performed if possible, with automatic switchover to LPR measurements in high electrolyte resistance situations or other conditions indicating possible inaccuracy in the HDA measurements. In this aspect, the processing system performs the HDA type measurements and computes a Stern-Geary constant (B value) based on the harmonics of current signals sensed by the sensing circuitry in each of a series of device cycles. One or more plausibility tests are then performed with respect to the computed B value, such as ascertaining the relative sizes of the computed electrolyte (electrolyte) resistance $R_S$ and a computed polarization resistance $R_P$ by determining whether the quantity $(R_S/(R_S+R_P))$ is less than a threshold (e.g., about 0.1 in one example), determining whether the quantity $(2I_1 I_3 - I_2^2)$ is greater than zero, and/or determining whether the computed B value is in a predefined range (e.g., about 10-60 mV in one embodiment). In one embodiment, if the plausibility test(s) indicates that harmonic distortion analysis is likely to yield an accurate corrosion related value, the processing system selectively computes the corrosion related value(s) using harmonic distortion analysis with the computed B value, and otherwise the corrosion value(s) is computed using LPR measurements with a user defined or default B value.

In accordance with other aspects of the invention, the processing system computes at least one statistical value using a running moment calculation in deriving the corrosion related value(s) using electrochemical noise (ECN) measurements, thereby mitigating the need to store large amounts of data and reducing the number of required computations in each device cycle.

In a related aspect, the processor is operative to compute a localized corrosion index based on a standard deviation of sampled current signals and on an rms of the sampled current signals, where the standard deviation and rms are both based on the running moment calculation.

Another ECN related aspect of the invention involves effectively shorting auxiliary and working electrodes by connection thereof to a circuit virtual ground during ECN measurements. In one embodiment, the processing system selectively reconfigures the switching components to connect the auxiliary and working electrodes to a virtual ground in the probe interface system, computes the corrosion related value(s) based on signals sensed by the sensing circuitry using ECN.

Further aspects of the invention relate to the use of linear polarization resistance (LPR) measurements in the device, where a calculated B value is employed rather than a predefined user B value. The computed B value, moreover, is preferably low pass filtered in certain embodiments, to facilitate noise immunity. In one embodiment, the processing system computes a B value based on harmonics of current signals sensed by the sensing circuitry in each of a series of device cycles, and computes the corrosion related value(s) in a given device cycle based on the computed B value and a current signal sensed by the sensing circuitry using a linear polarization resistance measurement.

BRIEF DESCRIPTION OF THE DRAWINGS

The following description and drawings set forth certain illustrative implementations of the invention in detail, which are indicative of several exemplary ways in which the various principles of the invention may be carried out. The illustrated examples, however, are not exhaustive of the many possible embodiments of the invention. Other objects, advantages and novel features of the invention will be set forth in the following detailed description of the invention when considered in conjunction with the drawings, in which:

FIG. 4 illustrates a table showing several exemplary switching system configurations for SRM, HDA, LPR, cell offset voltage, and ECN measurements in the device of FIGS. 1-3B;

FIG. 5 is a partial sectional side elevation view schematically illustrating the probe and electrodes of the measurement device installed in a pipe or storage structure with the electrodes exposed to a transported or stored electrolyte for corrosion measurement;

FIG. 6 is a simplified schematic diagram illustrating an equivalent circuit for one of the electrodes and the measured electrolyte in the installation of FIG. 5;

DETAILED DESCRIPTION OF THE INVENTION

Figure 1:
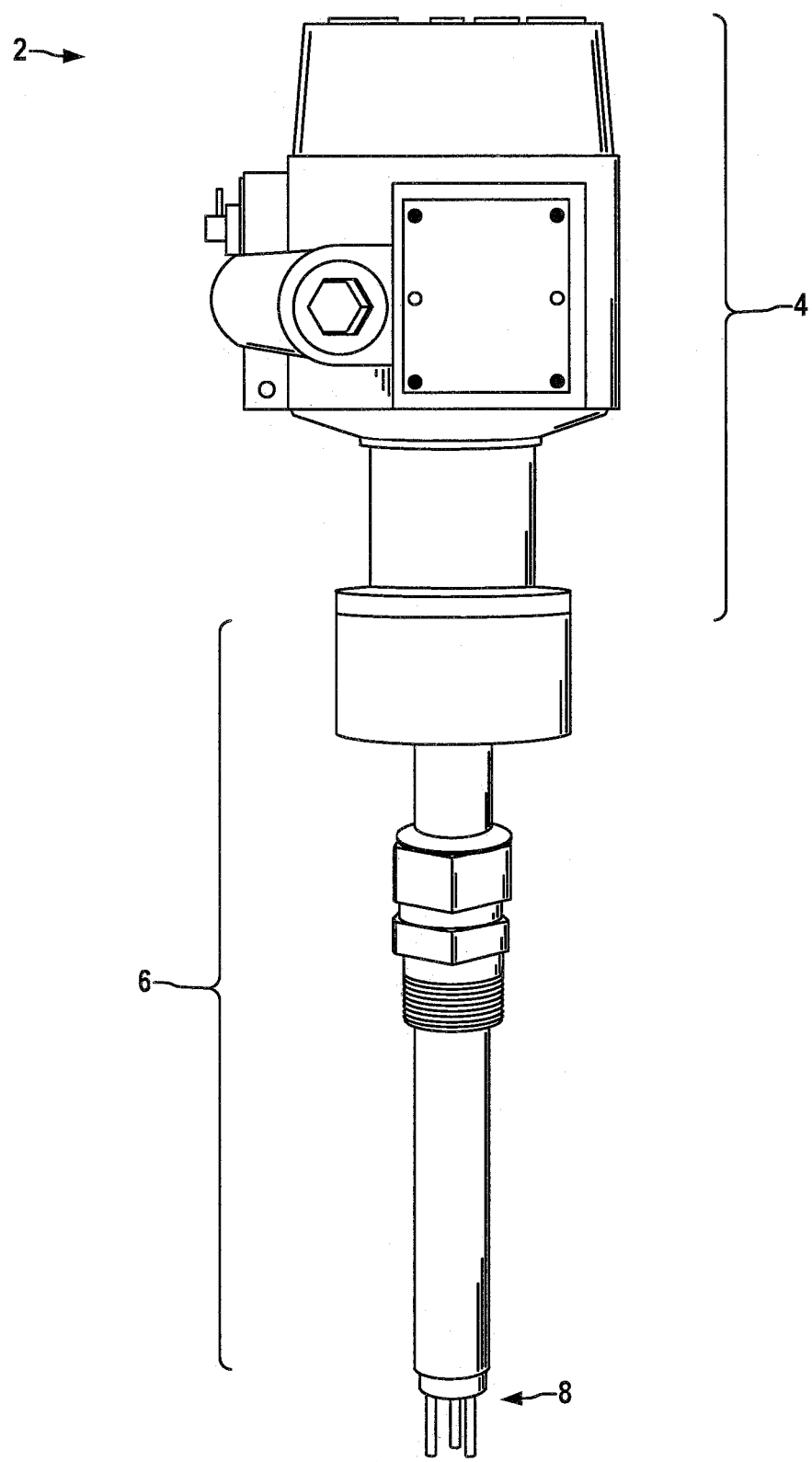
FIG. 1 is a perspective view illustrating an exemplary corrosion measurement device including a loop or battery powered transmitter with an associated probe and electrodes in accordance with one or more aspects of the present invention.

Referring now to the figures, several embodiments or implementations of the present invention are hereinafter described in conjunction with the drawings, wherein like reference numerals are used to refer to like elements throughout, and wherein the various features and plots are not necessarily drawn to scale. The invention relates to programmable low power corrosion measurement field devices for providing corrosion measurement and monitoring using one or more advanced corrosion measurement types to provide conductivity, general corrosion, and/or localized corrosion values for real time corrosion monitoring and/or off-line corrosion data logging which may be employed in distributed control systems connected by a standard 4-20 mA control loop or other communicative means, or which may act as stand-alone devices with the capability of downloading stored corrosion data to a user communications device.

Referring initially to FIG. 1, an exemplary field corrosion measurement device 2 is illustrated in accordance with one or more aspects of the invention, including a transmitter head 4 that houses the processor-based electronic circuitry as described in greater detail hereinafter, along with and a probe 6 and a set of three electrodes 8 which are preferably made of a material matching that of a metal structure into which the device 2 is installed for corrosion monitoring/measurement, where the electrodes 8 are immersed or embedded in the solution or other electrolytic solid, gas, or liquid stored or transported in the installed structure, such as a pipeline, storage tank, or other structure of interest. The transmitter housing 4 and the probe 6 are constructed of environmentally protective materials to allow use of the device 2 in field applications such as for online corrosion monitoring to generate process variables for corrosion rate, localized corrosion index (degree of corrosion localization), and/or electrolyte resistance (conductivity). In operation, the probe 6 is mounted to a structure of interest with the electrodes extending into the interior of a pipe or fluid chamber so as to be exposed to a corrosion process therein.

As set forth in greater detail below, the device 2 can perform a number of different corrosion related measurements, including measuring polarization resistance RP, solution resistance RS, and electrochemical noise measurements. Linear polarization resistance (LPR) measurement is a simple technique that works in most situations, in which a set voltage is applied to the test electrode and the resulting current is measured to derive a value for the polarization resistance $R_P$. The corrosion current $I_{corr}$ is then calculated from the polarization resistance RP (=applied voltage/flowing current) as $I_{corr}=B/R_P$, where B is the Stern Geary constant. LPR is affected by any significant solution resistance $R_S$ present (appears in series with $R_P$) and also by uncertainty in knowledge of the B value, and is generally quite robust and immune to noise etc. especially if done using a sine wave excitation as in the embodiments illustrated and described further below. Harmonic distortion analysis (HDA) calculates $I_{corr}$ directly from the harmonics of the resulting current (if the applied voltage is a pure sine wave), and does not require knowledge of a B value. Since $I_{corr}$ from LPR and from HDA should theoretically be the same, it is possible to calculate B from the harmonic information used in HDA computations based on a known or measured $R_P$. HDA is also affected by solution resistance $R_S$, which tends to 'linearize' the response, wherein harmonic distortion is the result of non-linear $R_P$, and not of $R_S$ which appears in series with $R_P$. Since the harmonics can be of low level, the measurement result ($I_{corrharm}$) from HDA can be disturbed by noise from one measurement to the next, and if the B value is calculated from a noisy $I_{corr}$ and from $R_P$, the computed B value will also be noisy. To address this situation, the values computed for $I_{corrharm}$ could be filtered or averaged, but this would slow down the response time of the device 2 and inhibit the ability to detect changes of the corrosion attack. To address these competing goals, the device 2 calculates an instantaneous B value for each measurement (from $R_P$ and $I_{corrharm}$), and averages the B fluctuations by digital low pass filtering, wherein the filtered computed B value can be used with the instantaneous $R_P$ to calculate $I_{corr}$. All the perturbative techniques for SRM, LPR, and HDA provide an average corrosion rate of the test electrode and are not very sensitive to localized corrosion. ECN, however, is also possible in the device 2, which provides a non-perturbative measurement technique (no externally applied excitation), which provides an indication of any localized corrosion. ECN, moreover, can detect electrochemically caused localized attack (pitting, crevice corrosion, etc.) as well as localized attack caused by mechanical damage to any protective oxide film naturally formed on the test electrode—such as cavitation damage, erosion damage, stress corrosion cracking etc.

Figure 2:
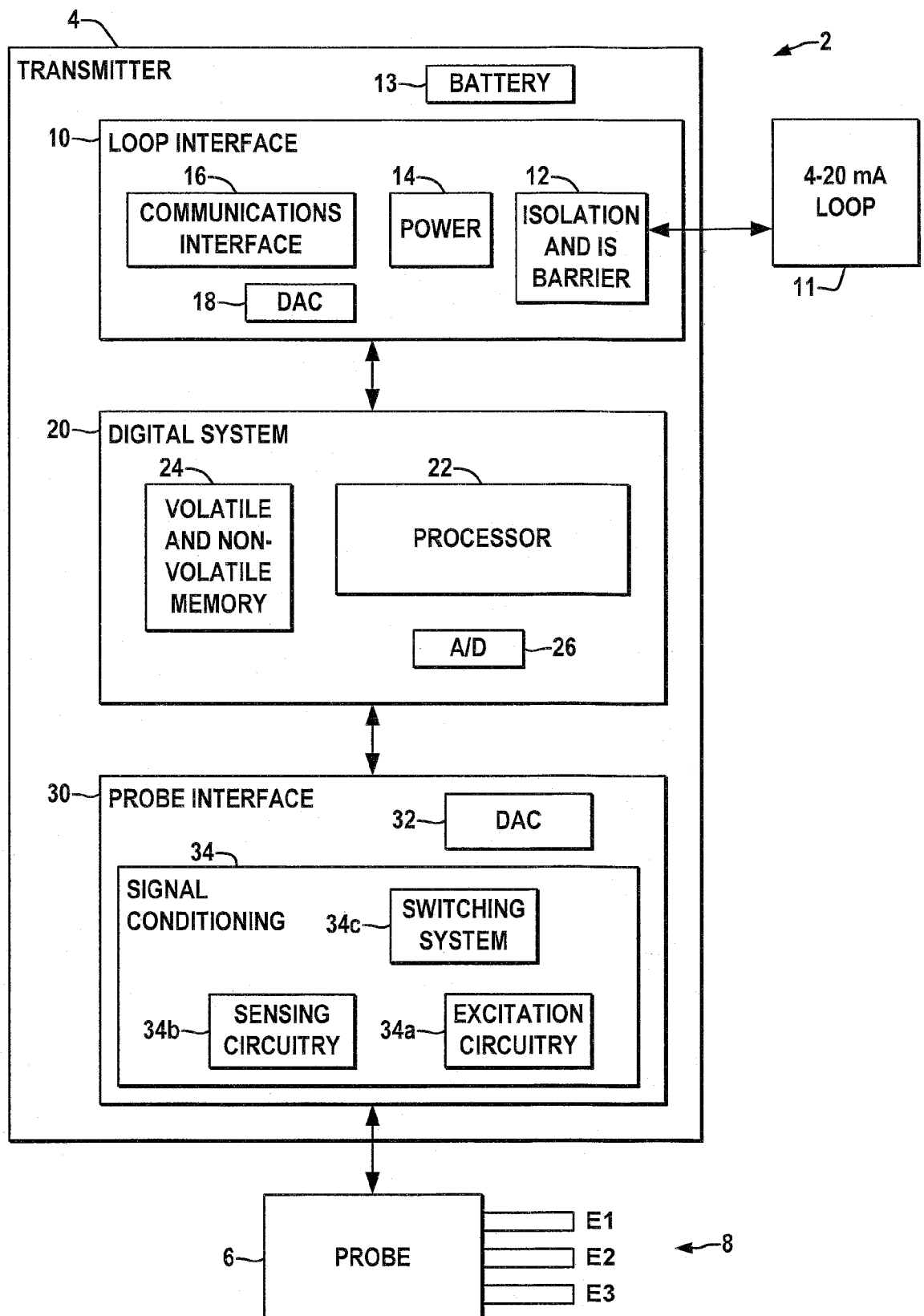
FIG. 2 is a schematic diagram illustrating further details of the transmitter of FIG. 1 including a digital system, a loop interface, and a probe interface.

Referring also to FIG. 2, the electronics of the transmitter 4 are schematically illustrated, which include a loop interface 10 with galvanic isolation and intrinsic safety (IS) barrier circuitry 12 through which the device 2 interfaces with a standard 4-20 mA control loop 11, and a power system 14 that provides internal device power derived from either current from the control loop 11 or alternatively from a battery 13, solar panel (not shown) or other source. The loop interface 10 further includes a communications interface 16 operatively coupled with a processor 22 of a digital system 20 and with the control loop 11 to allow the processor 22 to communicate using HART or other communications protocol(s) with an external communications device (not shown) by which a user may configure or program the device 2 and/or may retrieve stored computed corrosion related values from the device 20. The exemplary loop interface 10, moreover, includes a dedicated digital-to-analog converter (DAC) 10 for controlling the current in the loop 11 so as to allow the processor 22 to control current in the loop to indicate a measured/computed process variable (e.g., loop current level between 4 and 20 mA corresponding to corrosion rate, localized corrosion index, conductivity, etc.) and also provides for FSK or other type modulation of the loop current to perform digital communications via the loop 11 or other wired or wireless communications means according to a suitable protocol such as HART, etc.

The device 2 also includes a digital system 20 comprising a processing system 22, which can be any form of processing circuitry such as a microprocessor, microcontroller, digital signal processor (DSP), programmable logic, etc., by which the various functionality described herein can be accomplished. The digital system 20 includes one or more forms of memory 24, in particular, non-volatile memory such as flash, FRAM, etc., and may include an analog-to-digital converter (A/D) 26, wherein the A/D 26 and/or the memory 24 may be separate components or circuits, or may be integrated in the processor 22.

The corrosion measurement device 2, moreover, includes a probe interface system 30 with signal conditioning circuitry 34 to interface with a plurality of measurement electrodes 8 situated in the electrolyte to be measured. In the illustrated implementation, moreover, the probe interface 30 includes a second DAC 32 for generating excitation signals to be applied by the signal conditioning circuitry 34 to at least one of the electrodes 8 for certain measurement types as described further below, wherein the excitation DAC 32 may alternatively be located within the digital system 20 and may optionally be integrated with the processor 22. The signal conditioning circuitry 34 comprises excitation circuitry 34a that provides excitation signals according to the output of the DAC 32 to the electrolyte via a first electrode E1, also referred to as an auxiliary electrode, and sensing circuitry 34b is provided to sense one or more corrosion-related electrical signals, such as voltages, currents, etc., via one or both of the other electrodes E2 and/or E3, wherein the second electrode E2 is referred to herein as a reference electrode used for sensing voltage signals in the electrolyte, and the remaining electrode E3 is referred to as a work or working electrode for sensing current signals with respect to corrosion rate, wherein the reference and/or auxiliary electrodes E2, E1 can be made of inert material. The signal conditioning system 34, moreover, includes a switching system 34c with a plurality of analog switching components allowing processor controlled reconfiguration of the various components of the excitation circuitry 34a and the sensing circuitry 34b and the electrodes 8 in a plurality of different configurations.

Figure 3A:
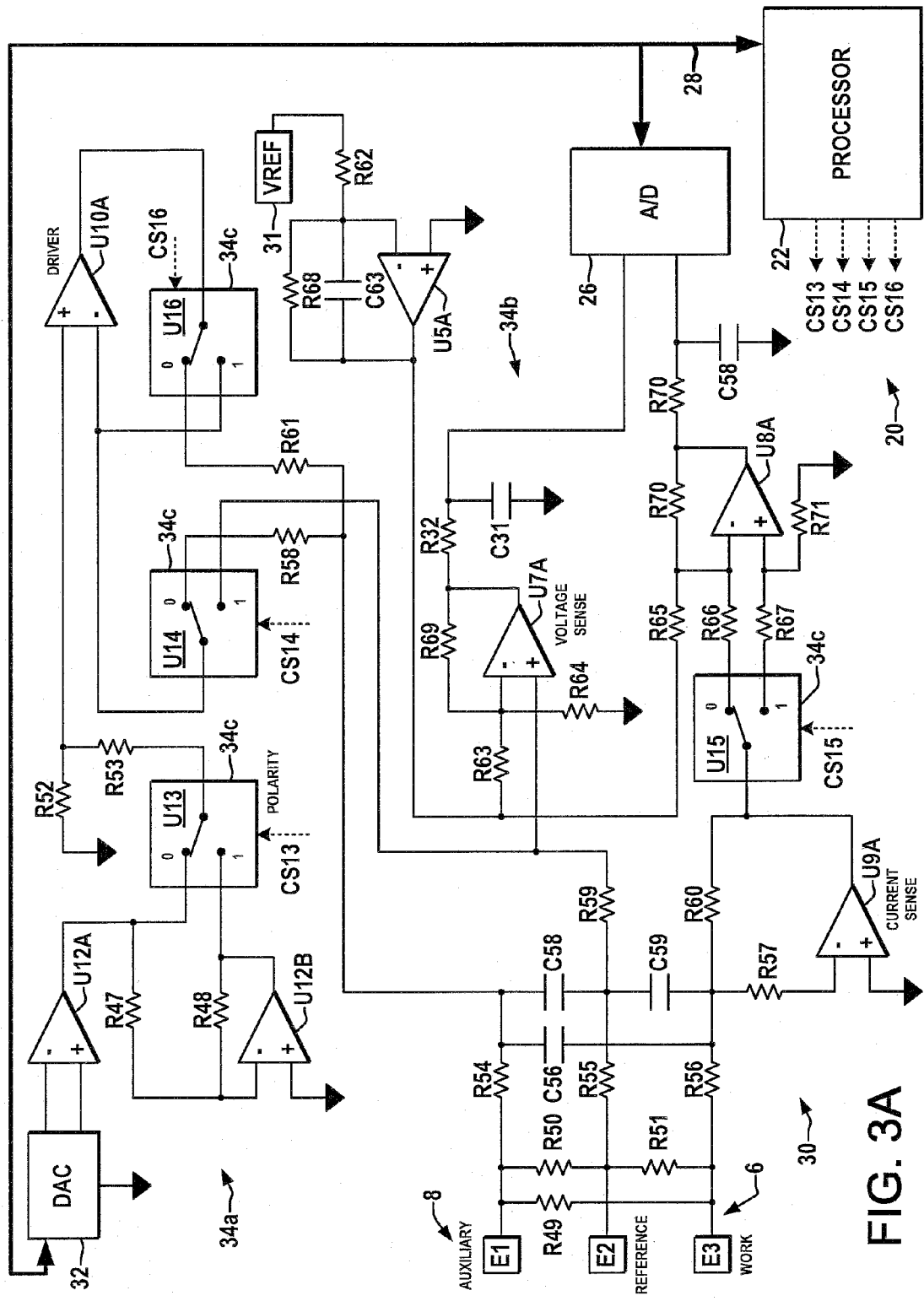
FIG. 3A is a schematic diagram illustrating portions of the probe interface system and the digital system in the exemplary transmitter of FIGS. 1 and 2 including processor controlled excitation circuitry, sensing circuitry, and an analog switching system for programmatic reconfiguration of the device for a variety of different corrosion measurements.
Figure 3B:
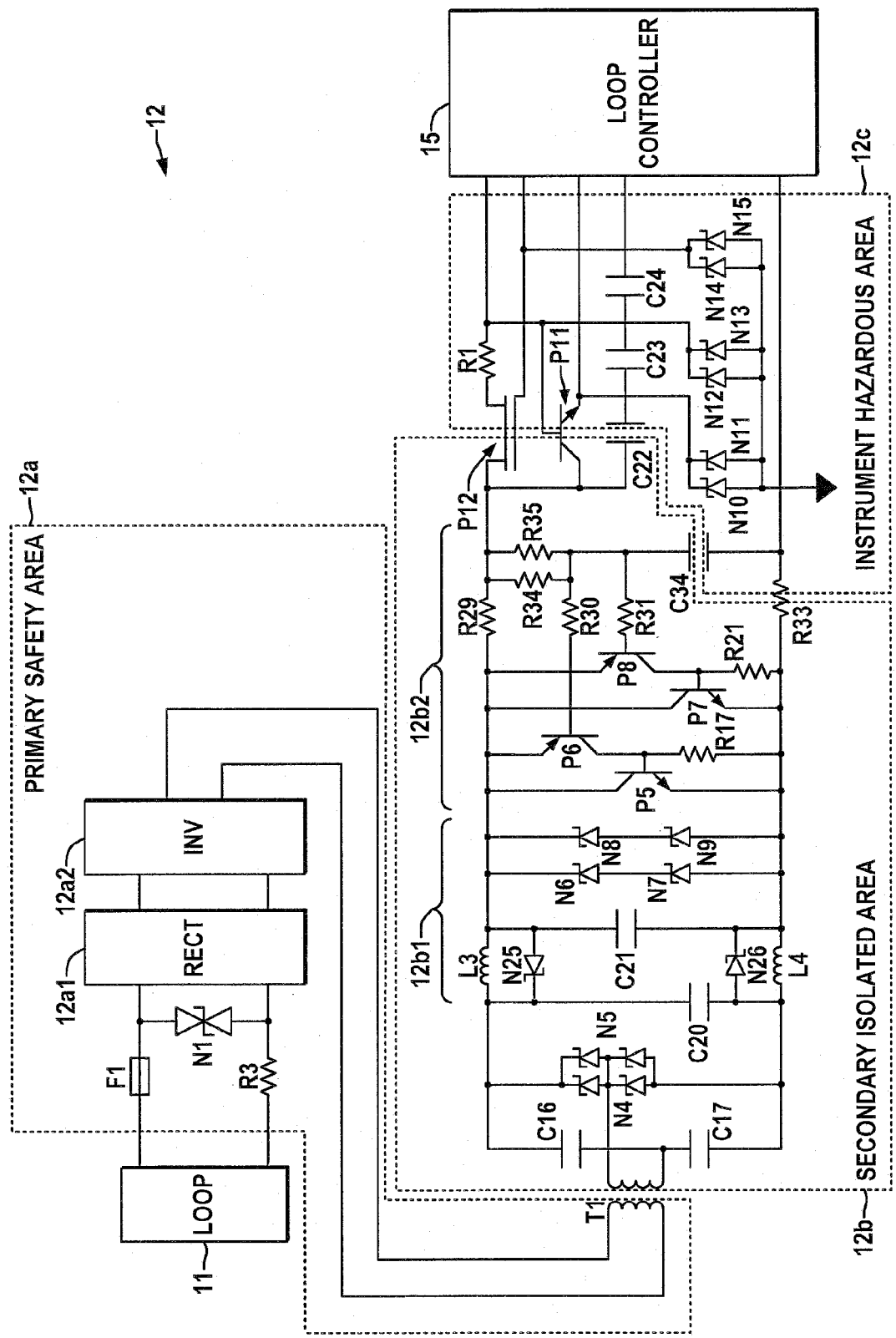
FIG. 3B is a schematic diagram illustrating further details of the isolation circuitry in the loop interface system of the exemplary transmitter of FIGS. 1 and 2 including an isolation transformer and a two stage intrinsic safety barrier.

Referring also to FIGS. 3A, 3B, and 4, further details of certain components of the probe interface system 30 and the digital system 20 are illustrated, including the excitation circuitry 34a, sensing circuitry 34b, and the switching system comprised of four analog switching devices 34c labeled U13-U16 in FIG. 3A. Each of the analog switches U13-U16 has two switching states, indicated in the figure as a "0" state and a "1" state, wherein the processing system 22 provides corresponding switching control signals CS13-CS16 to control the state of each switch 34c. The analog switches U13-U16, moreover, can have a third operational state controlled by a chip select input (not shown) in which the switch terminal is disconnected from either of the pole terminals. The switches U13-U16 are thus coupled for processor controlled interconnection of the components of the excitation and sensing circuits 34a and 34b to reconfigure the corrosion measurement device 2 in a number of different corrosion measurement arrangements, wherein FIG. 4 shows a table 70 illustrating the switch settings or states for SRM, HDA, LPR, Cell Offset Voltage, and ECN measurement operation of the device 2. The exemplary device 2 may be programmed by a user to operate in any single one of the measurement modes in FIG. 4 or may perform measurements in any combination of two or more of the listed measurement types in each of a series of device cycles, whereby the corrosion transmitter 2 is easily configured to accommodate any corrosion measurement or monitoring application. In this regard, the loop interface 30 allows for optimum interconnection of the signal conditioning circuitry and the electrodes 8 with respect to impedance and accuracy within the tight power constraints imposed by loop or battery power sources by minimizing the number of amplifiers and other components while providing advanced performance in terms of corrosion measurement and monitoring using ECN, HDA, SRM, LPR and Offset in a single user programmable device 2.

The processor 22 controls the excitation DAC 32 during each measurement period to provide suitable excitation to the cell via the excitation circuitry 34a, the first (auxiliary) electrode E1, and the switching system 34c, and also operates the measurement A/D 26 to obtain corresponding measurements of cell voltages and/or currents via the sensing circuitry 34b, the switches 34c, and the reference and working electrodes E2 and E3, respectively. The electrode couplings are made through the probe 6 with resistors R49-R51 and filter network R54-R56, C56, C57, and C58 forming the connection to the excitation and sensing circuitry 34a and 34b. In the scenarios described below, the device 2 performs a series of measurements in each device cycle through controlled switching of the devices U13-U16. In the illustrated device 2, moreover, certain of the selectable measurement types (e.g., SRM, HDA, and LPR) involve application of excitation signals, while others (e.g., ECN) do not, wherein general corrosion is computed using HDA or LPR measurement types, electrolyte resistance or conductivity is measured using SRM techniques, and ECN measurements are used in computing localized corrosion index values. In general, the excitation signals (if any) are applied to the auxiliary electrode E1 as voltage signals provided by the DAC 32 in either a first polarity using a first amplifier (e.g., opamp) U12A directly through the "0" state path of the switch U13 or in an opposite second polarity via an inverter configured amplifier U12B through the "1" state of the switch U13 with a driver amplifier U10A providing a corresponding output voltage to the auxiliary electrode E1 through the "0" state path of the switch U16 and a resistor R61. In these configurations, moreover, the electrodes are in the feedback loop of the driver amplifier U10A of the excitation circuitry 34a, whereby current flowing between the auxiliary and working electrodes E1 and E3 will cause the potential between the reference electrode E2 and the working electrode E3 to be the same as the applied excitation signal voltage. In certain operational configurations, moreover, no excitation is applied, wherein the switching system electrically isolates the auxiliary electrode E1 from the excitation circuitry 34a while the processing system 22 samples voltage signal sensed across E2 and E3 by the sensing circuitry 34b.

The return current resulting from any applied excitation voltage signals flows through the working electrode E3 in the exemplary three electrode potentiostatic measurement configuration, wherein the sensing circuitry 34b senses such currents via a current sense amplifier U9A forming a current to voltage converter with a current limiting resistor R57 current limiting resistor in a feedback path of the current to voltage converter, by which the current limiting resistance R57 (e.g., 1 kOHM in one embodiment) does not influence the current sensing operation. The resistance R57 of the current to voltage converter introduces a near zero voltage drop into the current path, and the value thereof may be selected to provide a gain according to requirements high signal sensitivity and wide dynamic range, and to protect the inverting input of U9A against overloads and is situated within the feedback loop of U9A so as to eliminate the effect of the resistance R57 on the current measurement. This current to voltage converter of the sensing circuitry 34b is used for sensing current in HDA and ECN measurements, and is also used in combination with a synchronous rectifier in measuring the polarization resistance LPR.

The current to voltage converter amplifier U9A provides an output to either an inverting input or a non-inverting input of amplifier U8A for the "0" and "1" states of the switch U15, respectively, where the output of U8A provides one of two inputs to the A/D converter 26 for current sensing. The current sense polarity switch U15 may thus be operated as a rectifier for certain measurement types to achieve toggled switching via the control signal CS15 from the processor 22. In this regard, when the excitation polarity switch U13 and the current sense polarity switch U15 are operated synchronously (by controlled switching of control signals CS13 and CS15 by the processor 22), these analog switching components constitute a synchronous rectifier used in certain embodiments for measuring the electrolyte (solution) resistance $R_S$ (SRM mode). The current sensing components, moreover, are employed without toggling of the polarity switch U15 for measurement of sensed currents from the working electrode E3 in performing HDA, LPR, and ECN measurements in the corrosion measurement device 2. The sensing circuitry 34b further provides voltage sensing capability with an amplifier U7A driving the second analog input of the A/D 26 for sensing the voltage at the reference electrode E2 through a high impedance path R59, which is compared with a reference voltage VREF 31 using amplifier U5A.

The A/D 26 can thus obtain and convert analog voltage and current values under control of the processor 22 and then provides digital values for these measurements to the processor 22. The A/D converter 26, moreover, can be any suitable conversion device, such as a delta-sigma modulator based converter in one embodiment, and is preferably operated at a relatively slow conversion rate. For example, the A/D 26 in the illustrated embodiments is operated to obtain measurement samples of the various corrosion related sensed signals at a sample rate significantly lower than the excitation signal frequency, such as less than about 10 samples per second, for example, sampling once every 300 msec in one embodiment, in order to remain within the power budget of the power system 14 for loop or battery powered implementations. The processing system 22 is thus operatively coupled with the probe interface system 30 to control the excitation signals provided to the electrolyte by the excitation circuitry 34a and to provide control signals CS13-CS16 to the switching system 34c to selectively reconfigure the switching components U13-U16 to perform a plurality of different corrosion measurement types and to compute at least one corrosion related value based on received measured values from the sensing circuitry 34b.

The circuitry of the transmitter 4 thus provides for application of excitation signals to the electrodes 8 via the probe 6, signal conditioning for sensing electrode signals, analog-to-digital conversion circuitry 26, and processing components 22 for controlling the application of excitation signals, obtaining signal measurements, and performing signal analysis to generate corrosion rate, electrolyte resistance or conductivity, and/or localized corrosion index process variables, in addition to 4-20 mA loop interfacing including support for HART communications. The device 2 may be configured to generate the 4-20 mA signal in the control loop 11 representative of a process variable, which may be a general corrosion rate in mils or mm per year indicating the current rate of an ongoing generally continuous corrosion process, an electrolyte resistance or conductivity value, or a pitting or localized corrosion factor, which is unitless and which represents a measure of the degree of localization in a process that may have a low corrosion rate, but which may lead to small but eventually deep holes in the pipe or tank material that reduce the material strength. The device 2 may also be configured to report one or more of these values through digital communications, either periodically or in response to data requests from another control entity on the loop 11 or from a user communication device.

Referring now to FIGS. 1-3B, the device 2 includes isolation and intrinsic safety (IS) barriers 12 providing galvanic isolation of the electrodes E1-E3 and the circuitry of the device 2 from the 4-20 mA loop. As shown in FIG. 3B, the current from the 4-20 mA loop 11 passes through an input stage of a primary safety area 12a with a fuse F1, a surge protector N1 and resistor R3 and a rectifier 12a1, followed by an inverter 12a2, which provides an input to an isolation transformer T1. The isolated output of the transformer T1 provides an input to a secondary isolated area 12b, including a voltage protection circuit 12b1 comprising voltage limiting zeners N6-N9 and current limiting circuits formed of transistors P5-P8 and resistors R17, R21, R29-30, R34, R35, and capacitor C34. The output of this first intrinsic safety barrier stage 12b provides an input to a second IS barrier stage 12c including further voltage limiting zeners N10-N15 thereby further limiting the possible voltage seen by a loop controller circuit 15. The IS protection of the device 2 also provides 1 KOHM protection resistors R57-R61 to protect the electrodes E1-E3. In operation, the measured electrolyte and the electrodes E1-E3 are typically connected to an earth ground, whereby the front end of the probe interface circuitry 30 is also grounded through a low impedance path. The isolation circuitry 12, and particularly the provision of the isolation transformer T1 mitigates or avoids potential ground loop problems through the 4-20 mA control loop 11 where multiple devices are installed in the same tank or pipeline. Thus, the device 2 may be used without external isolation components, thereby saving installation costs. Moreover, the isolation transformer T1 constitutes a component of the exemplary integral explosion prevention (intrinsic safety or IS) barrier. This dual stage IS circuitry 12b and 12c allows use of the device 2 in applications requiring intrinsic safety without the need for external IS circuitry, thereby further reducing installation costs. In these applications, for instance, the housing 4 (FIG. 1) is constructed as an explosion proof certified enclosure (e.g., for US) or indicated as "EX d" for Europe, and the provision of the internal IS circuitry in the device 2 allows connection thereof to a non-IS loop 11. In this manner, the exemplary device 2 effectively "converts" the Ex d or Explosion proof installation method to an IS protection for the electrodes 8 and the probe 6 (FIG. 1) without requiring an additional barrier.

Figure 7:
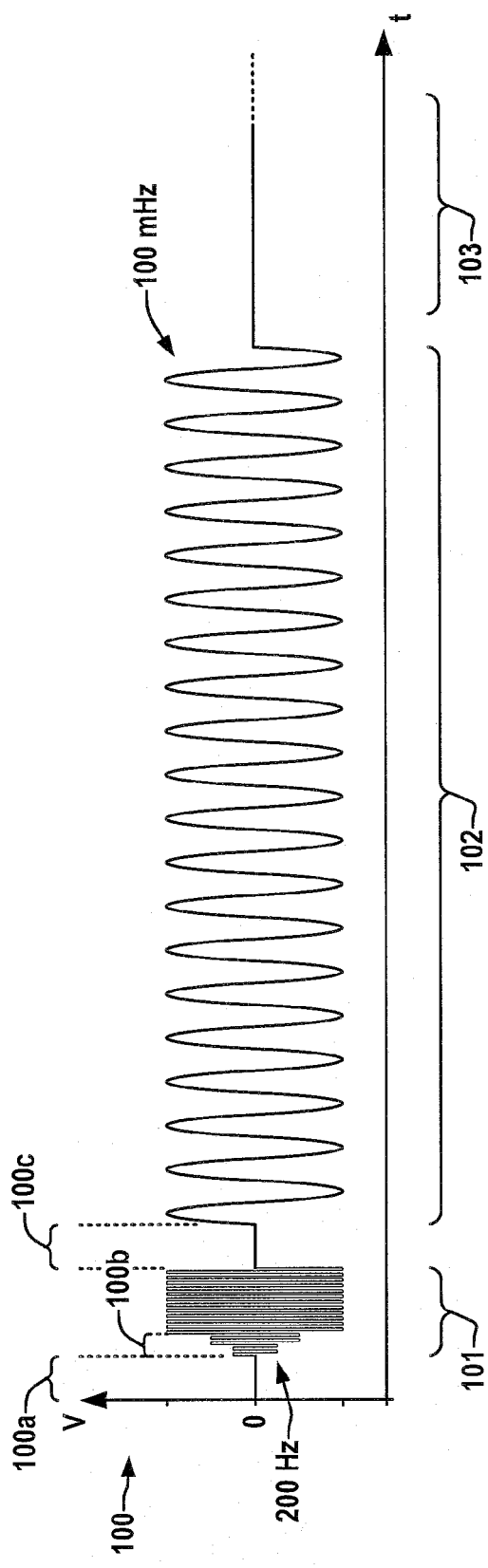
FIG. 7 is a graph illustrating exemplary excitation waveforms applied to the measured electrolyte by the excitation circuitry in a multi-phase measurement cycle of the device of FIGS. 1-6 including a substantially dc-free 200 Hz square wave for electrolyte resistance measurement, a 100 mHz sine wave for HDA and LPR measurements and an ECN portion with no excitation.

Referring also to FIGS. 5-7, in operation, the probe 6 is installed with the electrodes 8 being immersed in a electrolyte 50 being transported in a pipe or other metal structure 40, as illustrated in FIG. 5, wherein the electrodes may be of any geometry, including being flush mounted, and need not be in-line with one another, wherein the illustration of FIG. 5 is a schematic representation only. FIG. 6 shows an equivalent electrical circuit 60 for one of the electrodes E1 and the measured electrolyte 50 in the installation of FIG. 5, wherein the electrical circuits of the other electrodes E2 and E3 are equivalent to the circuit represented in FIG. 6. As shown in FIG. 6, the electrode/electrolyte circuit 60 includes the series combination of an internal cell voltage $V_C$ and a polarization resistance $R_P$ which are in parallel with electrochemical double layer capacitance Cdl between the electrode E1 and the electrolyte 50, where the electrolyte 50 has a resistance $R_S$ which is the subject of SRM measurements. As shown in an excitation signal graph 100 of FIG. 7, the signal measurements in one possible configuration of the transmitter device 2 are performed in three measurement periods 101, 102, and 103 that may alternatively be in any order in each of a series of device cycles, or the device 2 may be programmed to perform only one measurement per device cycle, or any combination of two or more measurement types in a given device cycle. In this configuration, the SRM measurement proceeds initially to provide the solution resistance value $R_S$, which is then used in the LPR or HDA measurements in determining the corrosion rate to correct for any errors in the computation of the polarization resistance $R_P$, as these resistances $R_S$ and $R_P$ are essentially in series as shown in FIG. 6.

In the first measurement phase 101 of the exemplary configuration shown in FIG. 7, a synchronous rectifier is operated initially in period 100a for offset measurement as described further below, after which the amplitude of the AC excitation signal is dynamically adjusted in period 100b. A relatively high frequency ac excitation signal is applied thereafter in portion 101 for solution resistance/conductivity measurement, followed by a gap 100c in which offsets are measured due to imbalances caused by non-identical electrodes 8. In the first phase 101, moreover, the device 2 advantageously applies an AC waveform with a mean of zero (substantially free of DC offset) to avoid polarizing the working electrode interface. Moreover, in the exemplary device 2, the DAC 32 and processor 22 are operated at low speeds (for power conservation), wherein the DAC output during SRM is set to a given dc level and the output polarity is switched using the switching system 34c to generate a bipolar square wave excitation signal for SRM measurements. In order to minimize the effects of possible small DC cell currents created by the SRM measurements in phase 101, the duration of the phase 101 is set to be as short as possible and the gap period 100c is provided with no polarization following the SRM measurements and before the LPR measurement in phase 102, thereby allowing the working electrode interface to depolarize.

In the first phase 101, the electrolyte (solution) resistance $R_S$ (and hence the electrolyte conductivity $1/R_S$) is measured using high frequency square wave excitation. In the second portion 102, the device 2 applies a lower frequency sine wave excitation voltage and measures current and the associated harmonics for determining the corrosion rate using LPR and/or HDA techniques. In the third portion 103, no excitation is applied, and the device measures electrochemical noise using ECN measurements for determining the localized corrosion index.

During the first portion 101 of the device cycle, the processor 22 causes the switching system 34c to configure the switches U13-U16 as shown in the SRM row of table 70 in FIG. 4, with U14 and U16 in the "1" switch states and with the synchronous rectifier operating with the switches U13 and U15 being toggled synchronously under control of the processing system 22 to provide a square wave excitation/current sense rectifier frequency of less than about 500 Hz, preferably about 100-200 Hz, wherein the graph 100 in FIG. 7 shows operation at a frequency of about 200 Hz in the first measurement period 101. It is noted in the equivalent circuit of FIG. 6 that application of a relatively high frequency (e.g., above about 50 Hz for example) will effectively short the upper leg because of the capacitance Cdl, wherein the resulting AC current sensed via the working electrode E3 will be inversely proportional to the electrolyte resistance $R_S$. Other waveforms could be used for the SRM measurement, such as sine waves, square waves, etc. The illustrated SRM measurement in period 101 involves provision of the square wave excitation voltage at the auxiliary electrode E1 together with the measurement by the sensing circuit 34b and the A/D 26 of the cell current sensed at the working electrode E3, wherein the DAC 32 (FIG. 3A) provides a DC output signal at a level controlled by the processor 22 with the switching of U13 alternating the polarity of the applied excitation voltage at the excitation frequency controlled by the processor 22 via control signal CS13. The resulting sensed cell current at the working electrode E3 will also be a square wave at the excitation frequency. The processor 22 also operates the current sense polarity switch U15 via signal CS 15 to toggle at the same frequency, whereby the sensed AC current signal will be rectified to present a rectified input signal to the A/D converter 26. In order to conserve power, the processor 22 controls the sampling of the A/D converter 26 at a much lower frequency, such as about 3.3 Hz in one embodiment. The processor 222 thus obtains many readings of the sensed current and averages these readings to compute the average sensed current, which is then used to compute the electrolyte resistance $R_S$.

Figure 8:
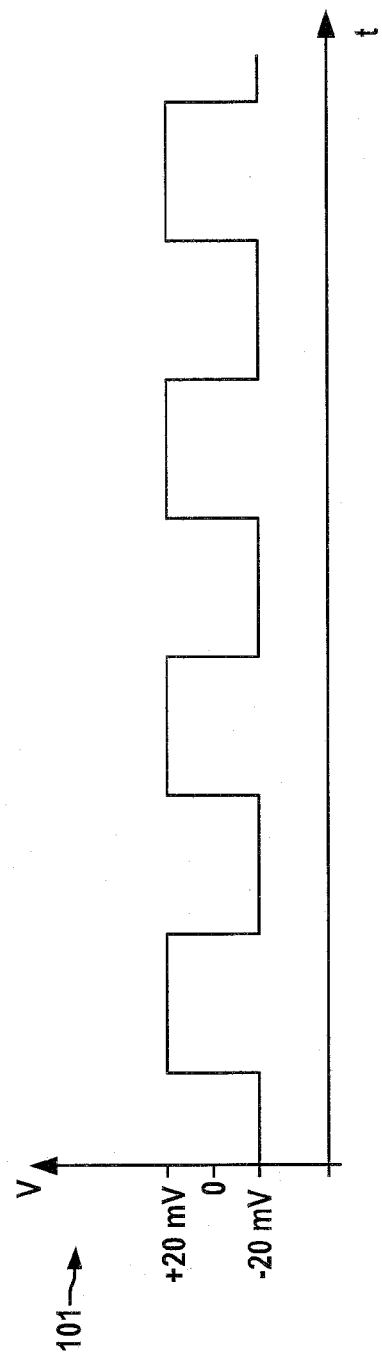
FIG. 8 is a graph further illustrating the substantially dc-free square wave excitation signal used in the device for electrolyte resistance measurements.

Referring also to FIG. 8, operation of the synchronous rectifier allows the provision of a substantially dc-free excitation signal to the auxiliary electrode E1 so as not to exacerbate corrosion in the cell, while the rectification of the sensed current signal via U15 allows the A/D converter 26 to be operated at a low sample rate and hence to conserve power, while taking enough samples to allow the processing system 22 to obtain an accurate average current value, wherein absent such rectification, the average current value would be zero or near zero. In this regard, it is noted that application of dc voltages to the auxiliary electrode alters the electrochemistry of the corrosion process being measured and may therefore interfere with any subsequent corrosion rate measurements. In addition, the rectification in the current sense circuitry will effectively eliminate any dc in the sensed current attributable to non-identical electrodes 8 by essentially chopping such dc component into an ac component with a mean value of zero. Moreover, the synchronous rectification also operates to reject interference at frequencies other than the switching frequency. FIG. 8 illustrates one possible substantially dc-free square wave excitation signal waveform applied during the first measurement period 101 by operation of the DAC 32 and the synchronous rectifier, having an amplitude of approximately +/−20 mV, wherein the DAC 32 of FIG. 3A provides a substantially constant dc value which is then polarity switched by toggling of the switch U13 to create the excitation waveform at the auxiliary electrode E1. The device 2 thus advantageously provides a non-intrusive dc-free square wave excitation signal in the first measurement period 101, while providing for synchronous rectification allowing slow sampling of the sensed current in performing SRM measurements within the limited power budget of loop or battery power along with rejection of dc and noise.

Figure 9A:
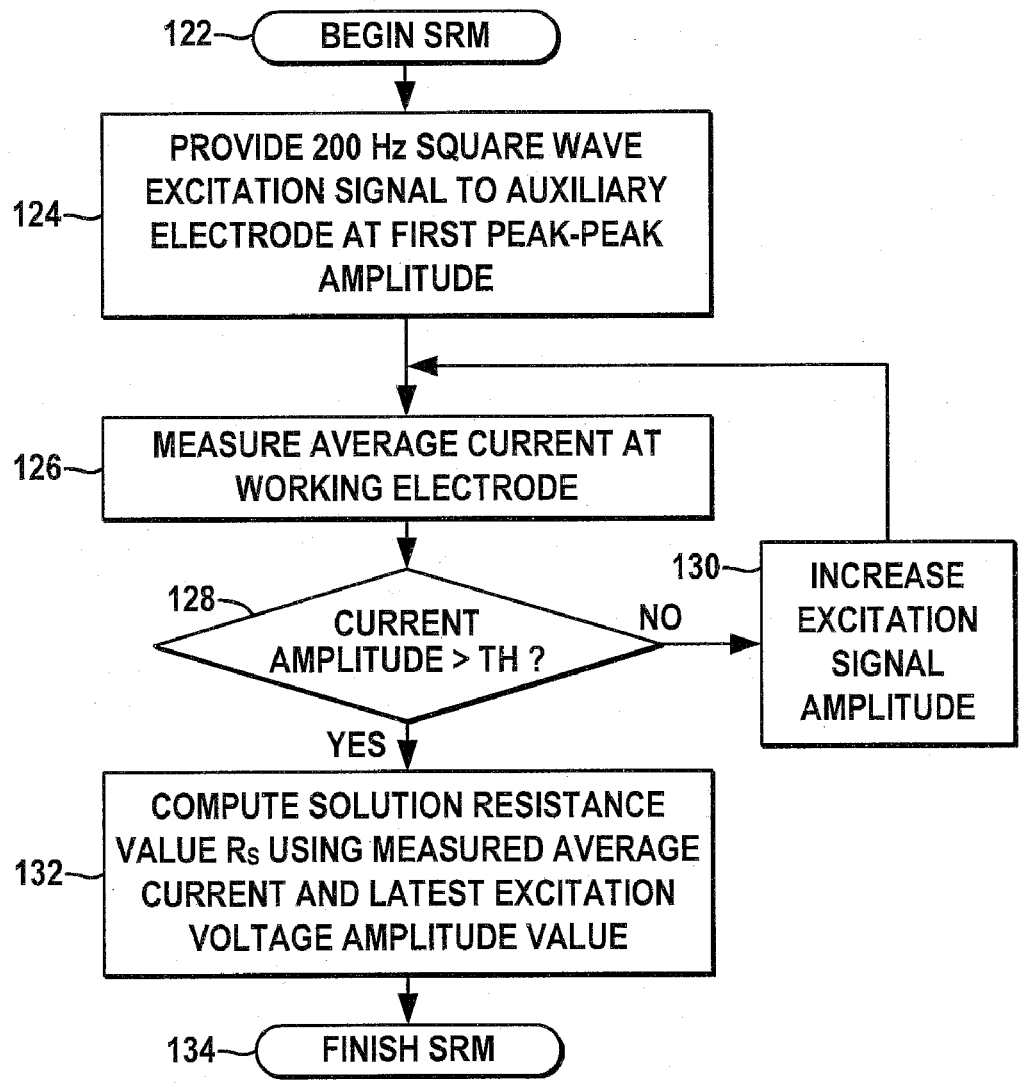
FIG. 9A is a flow diagram illustrating exemplary operation for electrolyte (solution) resistance measurement (SRM) using dynamic excitation amplitude adjustment in the device of FIGS. 1-6.
Figure 9B:
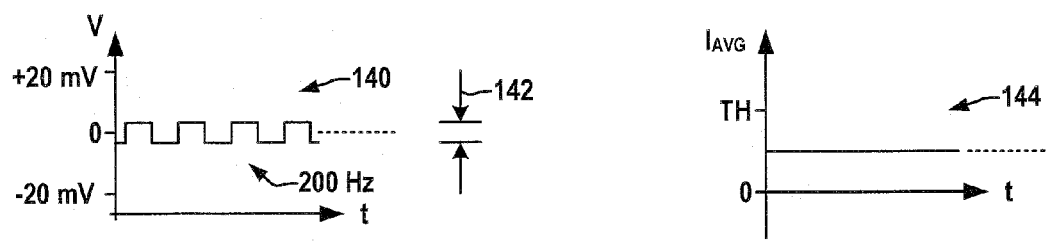
FIGS. 9B-9D are graphs showing voltage and current plots of square wave excitation voltages and corresponding measured average currents for different excitation waveform amplitudes during dynamic amplitude adjustment in the device of FIGS. 1-6.
Figure 9C:
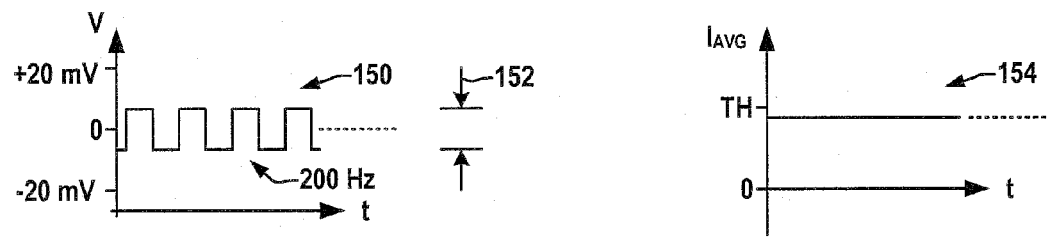
Figure 9D:
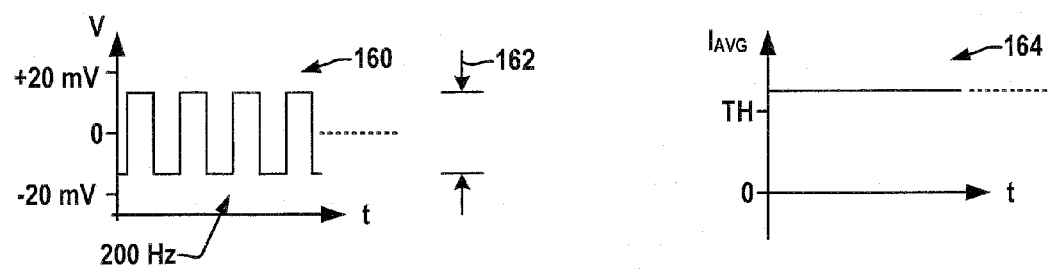

Referring also to FIGS. 9A-9D, the device 2 preferably adjusts the magnitude or amplitude of the square wave excitation signal in SRM measurements either at predefined time periods, or at the beginning of each SRM measurement period 101. This facilitates improved usage of the input range of the A/D converter 22, thereby facilitating improved accuracy in the measured current samples, and in the computed average current value and hence improved electrolyte resistance (or conductivity) measurements. A process 120 in FIG. 9A illustrates this exemplary operation, wherein the SRM cycle 101 begins at 122 and a relatively high frequency square wave excitation signal is provided at 124 to the auxiliary electrode E1 at a first (e.g., low) peak-to-peak amplitude. In one example, the square wave frequency is about 200 Hz, although other values may be used, preferably about 500 Hz or less. FIGS. 9B-9D illustrate graphs 140, 144, 150, 154, 160, and 164 showing voltage and current plots of square wave excitation voltages and corresponding measured average currents for different excitation waveform amplitudes according to the process 120 in FIG. 9A. In the first plot 140 of FIG. 9B, a square wave of about 200 Hz is applied at a relatively low first amplitude 142. The average current is measured at 126 in the process 120, for instance, by taking a plurality of measurements with the A/D 26 using the synchronous rectifier operation as described above or using other suitable techniques for measuring an average current value. A determination is made at 128 as to whether the average current value thus obtained exceeds a predetermined threshold TH, where any suitable threshold may be used by which a decision can be made regarding optimal usage of the A/D input range. In one example, the threshold is related to about half of the A/D input range although other values can be used.

If the measured current does not exceed the threshold TH (NO at 128), as shown in the current plot 144 of FIG. 9B, the excitation signal amplitude is increased at 130 (e.g., by increasing the output of the DAC 32 under control of the processing system 22), and the process 120 of FIG. 9A returns to again measure the average current at 126. This situation is shown in plots 150 and 154 of FIG. 9C, wherein the new excitation signal amplitude 152 is greater than the initial amplitude 142 of FIG. 9B. The new average current is compared with the threshold TH at 128, and as seen in the plot 154 of FIG. 9C, this current is still below the threshold TH. Accordingly, the process 120 of FIG. 9A again increases the excitation amplitude at 130 to a level 162 shown in the excitation voltage plot 160 of FIG. 9D. At this point, as shown in plot 164 of FIG. 9D, the latest excitation amplitude 162 provides for a resulting sensed average current that is greater than the threshold TH (YES at 128 in FIG. 9A), and the process 120 of FIG. 9A continues to 132 whereat the electrolyte resistance $R_S$ is computed using the latest excitation voltage amplitude value, and the SRM process in period 101 is finished at 134. In this manner, the corrosion measurement device 2 is adapted to utilize the full extent of the A/D conversion range, wherein the processing system 22 correlates the known latest excitation voltage amplitude with the latest measured and computed average current value at 132 to compute the electrolyte resistance $R_S$ and/or electrolyte conductivity. This adaptive adjustment of the excitation amplitude facilitates the optimal usage of the available A/D resolution, and provides for adaptation of the device 2 for applications having very low or very high electrolyte conductivities without sacrificing accuracy.

Figure 10A:
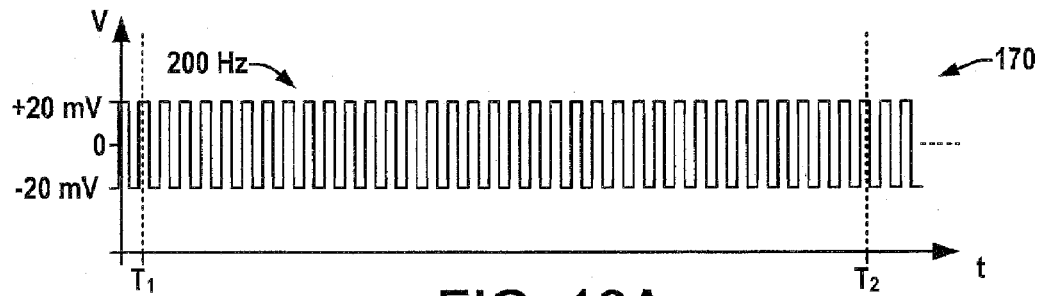
FIG. 10A is a graph showing a plot of an exemplary square wave voltage excitation signal applied at about 200 Hz and two exemplary asynchronous A/D converter samples using a low sample period of about 300 msec.
Figure 10B:
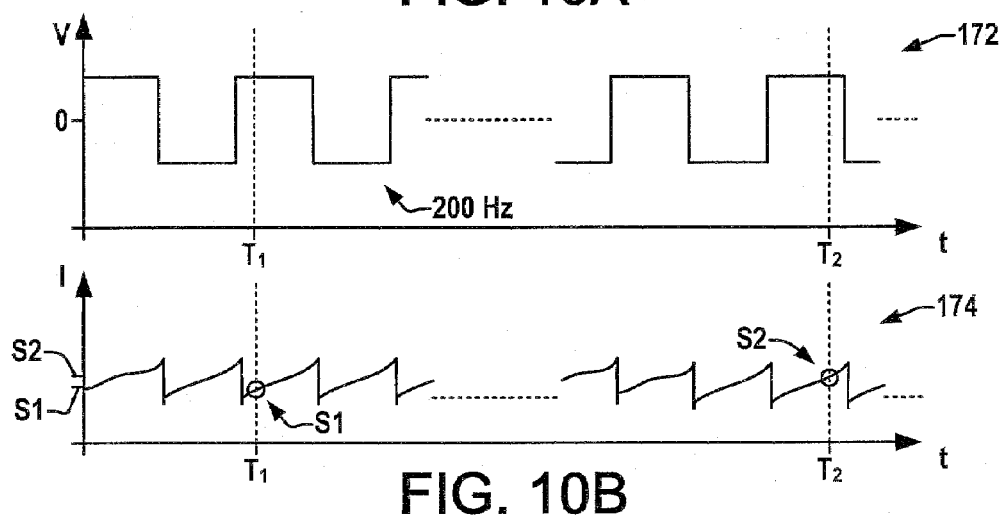
FIG. 10B is a graph showing excitation voltage and sensed current plots at the two exemplary sample times in FIG. 10A.
Figure 10C:
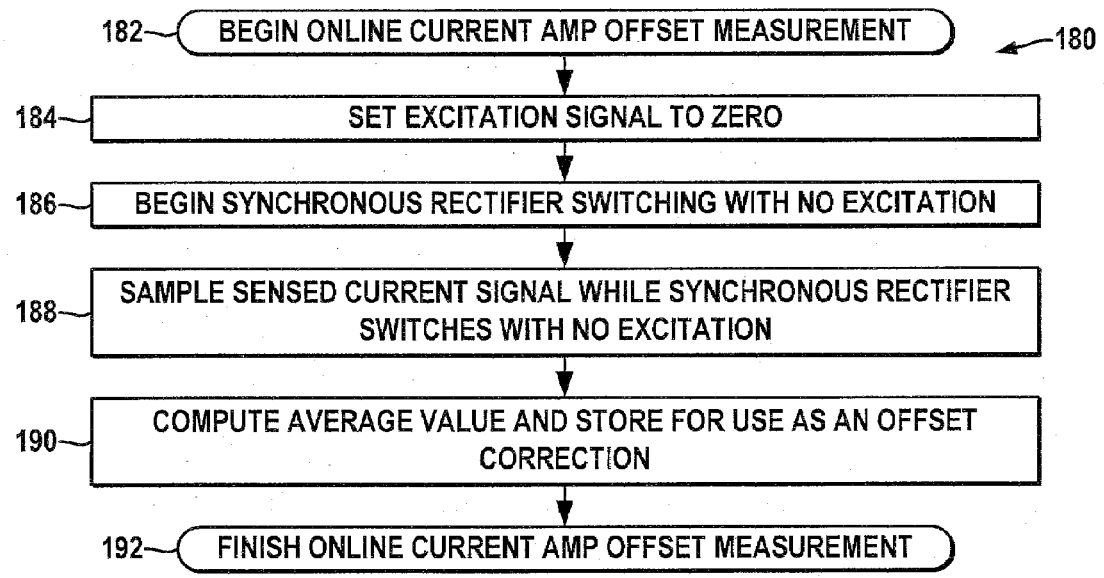
FIG. 10C is a flow diagram illustrating exemplary operation for online current amplifier offset measurement in the device of FIGS. 1-6.

Referring also to FIGS. 10A-10C, the device 2 also provides for calibration for current amplifier offset to further refine the accuracy of the computed corrosion related values. In this regard, the usage of the synchronous rectifier described above in conjunction with asynchronous A/D sampling may lead to situations in which the measured current and the input to the A/D converter 26 increase slightly during each cycle of the square wave as shown in FIGS. 10A and 10B. The plot 170 of FIG. 10A illustrates the 200 Hz square wave voltage excitation signal employed in SRM measurements along with two exemplary asynchronous A/D converter samples S1 and S2 at times $T_1$ and $T_2$, respectively, obtained using a long A/D sample period of about 300 msec. The graphs 172 and 174 in FIG. 10B show further details of the exemplary portions of the excitation voltage and sensed current plots, respectively, at the two exemplary sample times $T_1$ and $T_2$ in FIG. 10A, wherein it is seen that the first current sample S1 is somewhat lower than the second sample S2 simply because these were sampled at different points within the excitation cycle. In addition to these inaccuracies, offsets in the opamps U8A and U9A used to sense the current signals may contribute to reduced accuracy in computation of $R_S$, corrosion rate, and/or localized corrosion. Further inaccuracies may result from a dc offset difference between the inverting and non-inverting paths of the rectifier, the finite speed of the cell driver amplifier U10A, resistors and capacitors on the probe inputs.

In order to mitigate these inaccuracies, the device 2 provides for online current amplifier offset measurement, with an exemplary process 180 being illustrated in FIG. 10C. beginning at 182 by which the device 2 automatically determines an online offset value based on a measured current amplifier offset while the synchronous rectifier components U13 and U15 are toggled by the processor 22. At 184, the processor 22 causes the DAC 32 to set the excitation signal to zero, and begins toggling the synchronous rectifier components U13 and U15 via signals CS13 and CS15, respectively, at 184 with no applied excitation voltage, wherein the rectifier components are switched via signals CS13 and CS15 at the same rate as normally used for SRM measurements as described above (e.g., at about 200 Hz in on implementation). The processor 22 obtains a number of samples of the sensed current signal at 188 using the A/D 26 and computes an average current value at 190, which is then stored for subsequent use as an offset in the above described SRM measurements, and the online current amplifier offset measurement is finished at 192. Thereafter during the SRM measurements in period 101, the processor 22 uses the stored offset to correct the current readings before computing the electrolyte resistance value $R_S$, so as to counteract the adverse effects of offsets in the current sensing circuitry including amplifiers U9A and U8A and to compensate for sampling inaccuracies associated with the synchronous rectifier operation and the asynchronous sampling of the A/D converter 26.

Referring now to FIGS. 3A, 3B, 4, 7, and 11, the device 2 also provides for improved HDA and/or LPR measurement types, wherein FIG. 4 shows the switching system configuration for these modes with respect to the switch states of U13-U16 in FIG. 3A. The device 2 is thus configurable to compute a general corrosion rate $I_{CORR}$ using LPR or HDA techniques. Basic LPR measurements typically employ a default or user entered B-value, whereas the HDA approach involves calculation of a B-value and the corrosion rate at the same time according to measured current harmonics. However, the inventors have appreciated that the conventional HDA computations are not viable or robust in all corrosion applications, wherein the device 2 operates to selectively employ one or the other of these techniques (HDA or LPR) according to the results of online plausibility tests using the measured current harmonics and electrolyte resistance.

The second exemplary measurement portion 102 in FIG. 7 illustrates the excitation applied in this portion 102, in which a low frequency sine wave excitation voltage is applied to the cell via auxiliary electrode E1 for LPR or HDA type measurements of current harmonics. In these measurement types, the sinusoidal excitation signal is preferably at an excitation frequency of about 50 mHz or more to allow for measurement of current samples over more than one cycle of the excitation signal without unduly lengthening the device cycle time. Thus, in certain preferred embodiments, the excitation signal is provided at an excitation frequency of about 100-200 mHz, wherein the example of FIG. 7 uses an excitation frequency of about 100 mHz. Moreover, the processing system 22 in the preferred embodiments computes the corrosion related value(s) based on more than ten cycles, preferably about 20 cycles of the sensed sinusoidal current signal using harmonic distortion analysis or LPR in the second period 102. Thus, compared with conventional devices that measure current signals over only a single cycle with an applied excitation of 10 mHz, the illustrated device 2 provides improved ability to perform discrete Fourier transforms in the processing system 22 using data obtain across more than a single cycle, thereby improving the resulting corrosion related value computational accuracy. In this respect, the use of an exemplary excitation frequency of about 100 mHz with current signals sampled over about 20 cycles yields significant improvement, while only marginally increasing the duration of the second measurement period 102 for HDA or LPR measurements.

In the second period 102 of FIG. 7, the low frequency sinusoidal excitation causes a resulting sensed current signal having various frequency domain components, including a fundamental component at the excitation frequency and second and third harmonic components that are used for the corrosion related value computations in the processor 22. This harmonic information is obtained by sampling the sensed current signal and conversion thereof to digital data by the A/D 26, with the processing system 22 performing a discrete Fourier Transform (DFT) to generate a frequency domain spectrum for the sensed current. As discussed above, the exemplary embodiments of the device 2 sample the sensed current signals over more than one excitation cycle, and preferably use an excitation frequency greater than about 50 mHz, preferably about 100-200 mHz so as not to unduly extend the device cycle time, although the invention is not limited to these specific examples. From the DFT frequency domain spectrum, amplitudes of the fundamental and various harmonics are obtained, and the harmonic measurement data is used in calculating the corrosion rate. In one possible implementation, moreover, the DFT is computed in concert with the sine wave excitation voltage generation, wherein the sinusoidal excitation voltage is generated as a series of small steps by the DAC 32 (FIG. 3A) from a memory look-up table in the processing system 22 or the memory 24 (FIG. 2), with the same look-up table being used for the DFT computations. In this regard, the exemplary table uses 96 steps per cycle to keep the size of the table small, and also to allow division by 2, 3, and 4.

The DFT is done essentially 'on the fly' in the illustrated example, by multiplication of the current sample value by an appropriate number from the look-up table. Furthermore, the exemplary DFT computation calculates the real and imaginary components at each of the harmonics, and employs the modulus as the square root of the sum of the squares thereof (e.g., $(real^2 + img^2)^{1/2}$) as this is less sensitive to noise than selecting one or the other of the real and imaginary components. The fundamental and the 2nd and 3rd harmonic are computed by multiplying the A/D value by an appropriate value from the sine look-up table after each discrete sine step, and adding the result to the appropriate accumulator variable, wherein this approach mitigates the need for intermediate data storage. The output of the DAC 32 is preferably scaled using a resistive divider R52, R53 to decrease the size of the smallest single bit step, where the values of R52 and R53 may preferably be selected to cover the widest possible range of cell offset, while minimizing the single bit step size, and the processing system 22 may ensure that the cell offset and/or required perturbation amplitude do not exceed the available range. Furthermore, in the illustrated embodiments, sequence delays may be provided to allow for the effects of step changes in the sine output on the cell current to pass prior to cell current sensing/measurement by the A/D 26.

The excitation frequency is preferably selected to be less than the typical time constant of the corrosion process (e.g., Cdl in parallel with $R_P$) but high enough for a reasonable measurement time to obtain data from more than one excitation signal cycle. In this respect, sampling over a fairly large number of cycles at a somewhat higher frequency mitigates the amount of sampled discontinuities. For instance, if fairly slow signal drifting is occurring, a discontinuity will be sampled (e.g., a difference between the first and last samples) if data is only taken over a single cycle, where such discontinuity will result in a Fourier spectrum with excessive harmonic content, thereby adversely affecting the HDA measurement technique. Moreover, averaging over more than one cycle improves immunity to interference and noise.

In the illustrated implementation, the processing system 22 evaluates the following equations (1)-(3) in each device cycle using the harmonic data obtained in the measurement period 102 to compute the corrosion current $I_{corr}$, from which the corrosion rate can be determined:

$$I_{corrharm} = I_1^2 / ((48)^{1/2} * (2 * I_1 * I_3 - I_2^2)^{1/2}) \quad (1)$$

$$B_{HARM} = (I_{corrharm} * \text{Sine Amplitude}) / I_1) - (R_S * I_{corrharm}) \quad (2)$$

$$I_{corr} = ((B_{HARM} \text{ OR } B_{USER}) * I_1) / ((\text{Sine Amplitude}) - (R_S * I_1)) \quad (3)$$

, where $I_1$ is the fundamental component of the sensed current and $I_2$ and $I_3$ are the second and third harmonic components, respectively, Sine Amplitude is the amplitude of the sinusoidal excitation voltage signal applied in period 102, and B is the application specific corrosion process value in units of volts. Once the corrosion current $I_{corr}$ is computed, this can be multiplied by constants relating to the specific electrode size, the faraday constant, and the atomic weight of the material, to calculate the corrosion rate in mm or mils per year.

Figure 11:
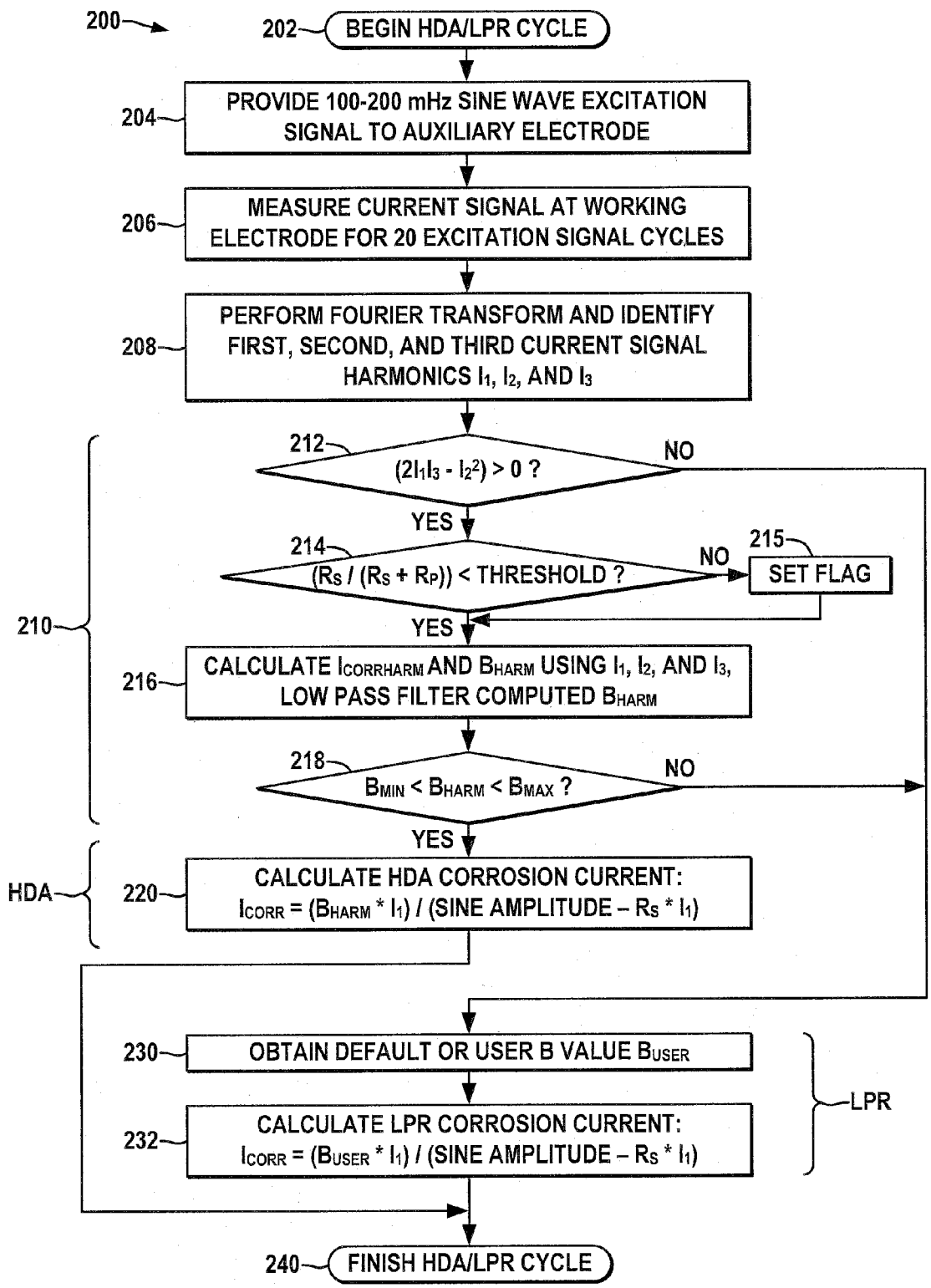
FIG. 11 is a flow diagram illustrating operation of the device for dynamic algorithm change for HDA or LPR measurement including plausibility testing of a computed B value in the device of FIGS. 1-6.

Referring also to FIG. 11, another feature of the exemplary corrosion measurement device is the computation of the B value $B_{HARM}$ based on the measured current harmonics $I_1$, $I_2$, and $I_3$ and the selective use of LPR or HDA algorithms based on the calculated $B_{HARM}$ value and the computed electrolyte resistance $R_S$. In this embodiment, HDA measurements and computations are performed if possible, and if the HDA results appear suspect based on one or more plausibility tests in a given device cycle, the processing system 22 changes to LPR type measurements. In particular, the device 2 automatically performs one or more of three types of tests to determine whether HDA computations are warranted and selectively changes the algorithm to LPR in high electrolyte resistance situations or other conditions indicating possible inaccuracy in the HDA measurements.

A dynamically changing HDA/LPR process 200 is shown in FIG. 11 beginning at 202 for the second period 102 in the exemplary device cycle of FIG. 7 above, wherein the processor 22 causes the DAC 32 and the excitation circuitry 34a to provide a sinusoidal excitation signal to the auxiliary electrode E1 at 204 and measures the current signal sensed at the working electrode E3 by the sensing circuitry 34b at 206 using the A/D converter 26. The processor 22 performs a DFT to identify the current harmonics $I_1$, $I_2$, and $I_3$ at 208 and then performs one or more tests at 210 to ascertain whether HDA corrosion measurements are plausible. In particular, a determination is made at 212 as to whether the quantity $(2*I_1*I_3 - I_2^2)$ is positive. If not (NO at 212), the HDA type measurement is deemed to be not plausible, since the square root of the tested quantity $(2*I_1*I_3 - I_2^2)$ appears in the denominator of the above equation (1). The process 200 continues to 230 in FIG. 11, whereat the processing system 22 obtains a default or user provided B value $B_{USER}$ and employs this in the LPR corrosion current equation (3) above at 232 to compute $I_{CORR}$ in the current period 102 whereafter the cycle ends at 240.

If, however, the first tested quantity $(2*I_1*I_3 - I_2^2)$ is found to be positive (YES at 212), the process 200 proceeds to 214 where a determination is made as to the relative size of the electrolyte resistance $R_S$ compared to the polarization resistance $R_P$ to determine whether the harmonics are accurately measurable, wherein high $R_S$ tends to linearize the cell response leading to low harmonic levels. In the illustrated embodiment, the quantity $(R_S/(R_S+R_P))$ is compared at 214 against a threshold, such as about 0.1 in one example, and if less than the threshold (NO at 214), the processor 22 decides that HDA may be suspect and sets a flag at 215 before proceeding to 216. Alternatively, the process may proceed to 230 to switch to LPR operation after the flag is set at 215. If the test at 214 does not indicate high $R_S$ (YES at 214), the process proceeds to a third test at 216, 218 with the processing system 22 computing $I_{CORRHARM}$ and $B_{HARM}$ at 216 by evaluating the above equations (1) and (2) using the measured current harmonics $I_1$, $I_2$, and $I_3$ and low pass filters the computed B value $B_{HARM}$. The computed B value $B_{HARM}$ in the illustrated example is low pass filtered digitally (e.g., moving average or other low pass type digital filtering performed by the processor 22), to remove any short term fluctuations and invalid readings, thereby extending the device sensitivity in situations where the measured harmonics may be of very low amplitude.

A determination is then made at 218 as to whether the computed B value $B_{HARM}$ is in a specified presumed valid range between a minimum value $B_{MIN}$ and a maximum value $B_{MAX}$, such as between about 10-60 mV in one example (e.g., or other range known to be viable for aqueous electrochemistry). It is noted that the exemplary low pass filtering of the computed B value $B_{HARM}$, such as a moving average or other digital filter, advantageously operates to remove any short term fluctuations and occasional rogue readings, whereby the device sensitivity may be enhanced with respect to low amplitude harmonic situations by using the filtered or smoothed computed B value. In one example, the filtered value $B_{HARM}$ is computed as $(1-X)*B_{HARM(n-1)}+X*B_{HARM(n)}$, where X in one implementation is about 0.05. If $B_{HARM}$ is not in the test range (NO at 218), the HDA technique is suspect, and the process 200 proceeds to 230 and 232 as described above. Otherwise (YES at 218), the processing system 22 calculates the corrosion current at 220 using HDA techniques by evaluating the above equation (3) using the computed B value $B_{HARM}$.

Yet another feature of the corrosion device 2 is the ability to utilize the computed B value $B_{HARM}$ (e.g., preferably low pass filtered) in performing LPR type measurements instead of a predefined user B value $B_{USER}$. In one embodiment, the processing system computes a B value based on harmonics of current signals sensed by the sensing circuitry in each device cycle according to the above equation (2) and computes the corrosion related value(s) using equation (3) based on $B_{HARM}$. In addition, the user may configure the device 2 for LPR measurements using a user B value $B_{USER}$, which may be obtained by any suitable means such as correlating weight loss data from test coupons, electrical resistance probes or wall thickness measurements, with LPR readings, wherein the computed B value $B_{HARM}$ may be monitored by a user or DCS to which the device 2 is connected. In this regard, observed changes in the computed B value $B_{HARM}$ may indicate changes in process electrolyte composition changes or other process events of interest from a process control/monitoring perspective.

Figure 12:
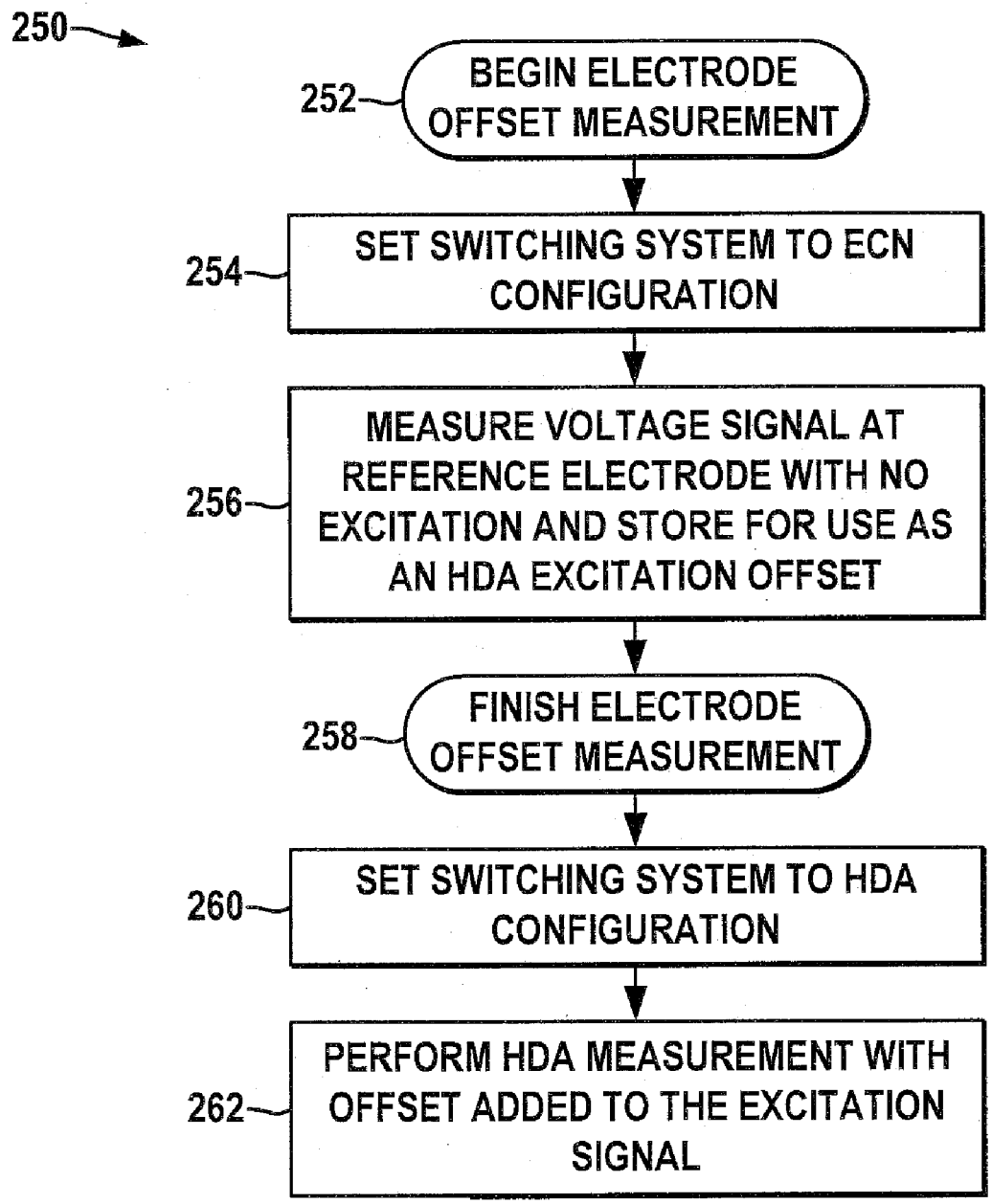
FIG. 12 is a flow diagram illustrating exemplary offset measurement and excitation signal adjustment for HDA corrosion measurement in the device of FIGS. 1-6.

Referring also to FIG. 12, another feature of the device 2 is the adjustment of the sine wave HDA/LPR excitation signal to compensate for differences in the electrodes 8. In this regard, in the ideal cell with identical electrodes 8, no net dc current would flow between the electrodes over a whole cycle of a sine wave excitation, in which case, the electrochemistry of the working electrode E3 would not be disturbed. However, assuming non-identical electrodes 8, a goal is to ensure that when no excitation is applied by the device 2, the current through the working electrode E3 is zero. Since the electrodes 8 are in the feedback loop of the driver amplifier U10A, the current flowing from the auxiliary electrode E1 to the working electrode E3 causes the potential between the reference and working electrodes E2 and E3 to be the same as that of the applied excitation.

In the example of FIG. 12, the processing system 22 switches the analog switches at 254 to the states indicated for ECN measurement in the table 70 of FIG. 4. Thus configured, the voltage signal at the reference electrode E2 is measured at 256 with no excitation, and is stored for use as an excitation offset during the HDA measurements, whereupon the online electrode offset measurement is finished at 258. Thereafter, the switching system 34c is switched at 260 by the processor 22 to the HDA configuration shown in the table 70 of FIG. 4, and the HDA measurements are taken at 262 with the offset value added to the excitation signal by the DAC 32 under control of the processor 22. In this manner, the device 2 performs the HDA measurements during the second measurement period 102 of FIG. 7 using the offset so as to compensate for any inaccuracies otherwise attributable to differences between the electrodes 8. By measuring the cell offset before the HDA is performed and adding the measured offset to the applied sine wave, any currents that are caused by the electrode differences are effectively eliminated during HDA measurement, whereby the device compensates for physical differences between the electrodes E1-E3 and thus increases accuracy and reliability of the HDA corrosion rate results. With respect to measurements at the working electrode E3, error currents attributable to electrode differences are believed to appear when polarization is applied, wherein providing the compensatory offset allows the working electrode E3 to be polarized about its free corrosion potential (Ecorr) as measured with respect to the reference electrode (RE), rather than about some other potential, thereby improving overall corrosion measurement accuracy.

A third measurement portion 103 of the exemplary device cycle shown in FIG. 7 employs detection of spontaneous noise with no external excitation for ECN type measurements. In this measurement mode, the device 2 measures sensed current (and voltage), and calculates statistical parameters based thereon, including mean, standard deviation ($\sigma$), and rms in certain embodiments, and further computes these statistics from statistical 'moments' of the data. Where used, the voltage or potential noise is measured between the reference electrode E2 and circuit ground, where the auxiliary and working electrodes E1 and E3 are effectively connected by the switching system 34c to a virtual ground. The statistical moments themselves may be computed from a complete data set (e.g., many samples of voltages and currents measured over a period of time), but such an approach would involve extensive computational overhead in the processor 22 and high memory usage. In preferred embodiments, therefore, a 'running moment' approach is employed so as to require significantly less memory. In the illustrated implementation, the processor 22 computes the first two statistical moments of the noise data for both current and voltage or for current alone, from which the statistics for mean, standard deviation, and rms are calculated, and used in the on-line electrochemical noise (ECN) measurements. The ECN is advantageously employed in the device 2 for computing a noise index or localized corrosion index value, wherein any form of such localized corrosion index may be computed in the device 2 which is indicative of the propensity of the electrodes 8 to localized corrosion attack in a given electrolyte. In one embodiment, a dimensionless localized corrosion index number is computed, which, when exceeding a certain level, indicates the possibility of localized corrosion attack occurring in a given installation. The device 2, in one embodiment, provides the localized corrosion index value as the ratio of the current noise standard deviation $\sigma_i$ to the current noise rms value ($rms_i$), which value is between 0 and 1, wherein high $\sigma_i$ values and low dc current values (usually seen with pitting attack) will result in a high (near 1) values for the localized corrosion index. Low uniform corrosion (low $\sigma_i$ and low dc currents) on the other hand correspond to localized corrosion index values near zero. In one possible implementation, a threshold value of 0.3 can be used as a warning limit, over which a possible localized corrosion attack may be indicated to the user, although any suitable index (unitless or otherwise) and corresponding comparison values may be selected.

Current noise is sampled in the device 2 via the working electrode E3 and a weighted average or running moment is computed, with the current noise statistics being used to compute the localized corrosion index. In one embodiment, moreover, the voltage (potential) noise may likewise be measured using the voltage sensing circuitry of the probe interface 30 and a second input channel to the A/D 26. In one preferred implementation, the device 2 uses running moment calculations in computing rms or standard deviations in deriving the localized corrosion index or other statistical measure. In this manner, the device 2 does not need to store large amounts of data and the number of required computations in each device cycle is reduced. In one implementation, the noise statistics are computed as running moments for each A/D sample and the process repeats until a certain number of samples "n" have been obtained, such as 1000 in one example. In this case, two moment variables M1 and M2 are initialized to zero by the processing system 22, and a variable for n is set to 1. The processor 22 then sets the switching system to the ECN configuration, and the sampled current and voltage measurements are incorporated into running computations to update the moment values at each sample time. The following equations provide for updating the moments with xn being the present current sample value and n being the present sample number (e.g., n ranges from 1 through 1000 in this example):

$d = (xn - M1)$ $M2 = M2 + (1/n)*(d^2(1-(1/n))-M2))$ $M1 = M1 + (d/n)$

In this implementation, moreover, similar computations are made for voltage samples obtained concurrently with the current samples, where the processing system 22 computes the moving moment values M1 and M2 for the voltage noise as well. Moreover, the above calculations are preferably optimized for execution time and memory use, such as by precalcualting certain common factors like (1−1/n) for each pass, wherein the calculations of M2 and M1 are done in the order indicated above for each sample cycle until the predefined number of readings (e.g., n=1000) have been obtained for both current and voltage readings. Thereafter, the current statistics may be computed as follows:

Mean = M1

Current standard deviation $\sigma_i = (M2)^{1/2}$

Current rms value $rms_i = (M1^2 + M2)^{1/2}$

Current noise index $= (M2/(M1^2 + M2))^{1/2}$

The processor 22 similarly computes like statistics for the voltage noise and then computes the current corrosion noise $I_{cornoise}$ as:

$I_{cornoise} = ((B_{HARM} \text{ OR } B_{USER})*\sigma_i)/(\ln(10)*\sigma_V)$

In another possible embodiment, the processor 22 computes a localized corrosion index based on a standard deviation of sampled current signals and on an rms of the sampled current signals, where the standard deviation and rms are both based on the running moment calculation. In this implementation, the voltage signals need not be sensed, and the corresponding voltage noise statistics need not be computed for localized corrosion measurement, thereby reducing the computational and memory storage overhead for the processor 22. In this approach, the moments M1 and M2 are computed for the measured current noise (with no excitation), and the current noise index $I_{cornoise}$ is computed as:

$I_{cornoise} = \sigma_i / rms_i = (M2/(M1^2 + M2))^{1/2}$

Another feature of the device 2 involves effectively shorting the auxiliary and working electrodes E1 and E3 by connecting these to a virtual ground of the probe interface system 30 during the ECN measurements. In one embodiment, the processing system selectively reconfigures the switching components U13-U16 as shown in the ECN entry of table 70 in FIG. 4, by which the auxiliary electrode E1 is connected through resistors R54 and R58 and through the "0" state of switch U14 to the inverting input of amplifier U10A providing a virtual ground, and the working electrode E3 is connected through resistor R56 to the virtual ground at the inverting input of U9A, as shown in FIG. 3A during the ECN measurements in the third measurement period 103 while the processor 22 performs the above measurements and calculations. For the ECN measurement, the auxiliary and working electrodes E1 and E3 are effectively shorted (e.g., with zero ohms therebetween) while still operating for measurement of current flowing between them via the current to voltage converter in the sensing circuitry coupled with the working electrode E3, including current limiting protection resistor R57. In this regard, the exemplary sensing circuitry 34b includes this resistance (e.g., about 1 KOHM in one embodiment) in the feedback loop of the amplifier U9A and is thus not seen by the flowing current.

Another advantageous feature of the device 2 is the adaptability for operation as a stand-alone data acquisition and storage device, which may be loop powered via a 4-20 mA control loop 11 or may be battery powered via battery 13 in FIG. 2, wherein the battery 13 may be chargeable by solar panels or other means. In this regard, the processing system 22 computes corrosion related values such as $R_S$, corrosion rate, localized corrosion index, etc., as described above, in each of a series of device cycles and stores the computed values in the non-volatile memory 24 (FIG. 2) for subsequent retrieval by a user. The device 2 is accessed by a user communications device (not shown) through the control loop 11 or by other wired or wireless means to allow downloading of the accumulated corrosion data, for instance, using HART or other suitable communications protocol(s). The device 2, moreover, is operable to store one or more day's worth of computed corrosion related values, such as over 5 days worth of data at long device cycle times in the illustrated embodiment. In this respect, for shorted cycle times, more data could be stored, such as several months or even years worth of data. This feature is advantageous in remote applications where the device 2 may be isolated from a distributed control system, and may operate on battery or solar power independently to acquire corrosion information for several days at a time, which data can then be read from the device 2 in a few minutes and thus stored in an external user communications device for transfer to a spreadsheet or to another system for further evaluation, wherein the battery 11 may be charged by solar panels connected to the device 2 in certain implementations.

The above examples are merely illustrative of several possible embodiments of various aspects of the present invention, wherein equivalent alterations and/or modifications will occur to others skilled in the art upon reading and understanding this specification and the annexed drawings. In particular regard to the various functions performed by the above described components (assemblies, devices, systems, circuits, and the like), the terms (including a reference to a "means") used to describe such components are intended to correspond, unless otherwise indicated, to any component, such as hardware, software, or combinations thereof, which performs the specified function of the described component (i.e., that is functionally equivalent), even though not structurally equivalent to the disclosed structure which performs the function in the illustrated implementations of the invention. In addition, although a particular feature of the invention may have been disclosed with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising".

Having thus described the invention, the following is claimed:

1. A loop-powered corrosion measurement device for measuring or monitoring corrosion of a structure exposed to an electrolyte, comprising:
   a loop interface coupleable to a 4-20 mA loop and comprising a power system to power the device using power from the 4-20 mA loop;
   a probe interface system with signal conditioning circuitry to interface with a plurality of measurement electrodes situated in the electrolyte, the signal conditioning circuitry comprising:
      excitation circuitry operative to provide an AC excitation signal to the electrolyte via a first one of the electrodes, and
      sensing circuitry operative to sense one or more corrosion-related electrical signals via at least a second one of the electrodes; and
   a processing system operatively coupled with the probe interface system to control the excitation signal provided to the electrolyte and to compute an electrolyte resistance value in each of a series of device cycles based on signals sensed by the sensing circuitry, wherein the processing system provides the excitation signal at a first amplitude and selectively increases the excitation signal amplitude until a resulting sensed signal exceeds a predefined threshold value.

2. The corrosion measurement device of claim 1, wherein the excitation signal is a substantially dc-free AC signal at an excitation frequency of about 500 Hz or less.

3. The corrosion measurement device of claim 2, wherein the excitation signal is a square wave signal.

4. The corrosion measurement device of claim 3, wherein the excitation signal is a substantially dc-free square wave signal at an excitation frequency of about 100 Hz or more.

5. The corrosion measurement device of claim 4, wherein the excitation signal is a substantially dc-free square wave signal at an excitation frequency of about 200 Hz.

6. The corrosion measurement device of claim 1, wherein the excitation signal is a square wave signal.

7. The corrosion measurement device of claim 6, wherein the excitation signal is a substantially dc-free square wave signal at an excitation frequency of about 100 Hz or more.

8. The corrosion measurement device of claim 1, wherein the excitation signal is a substantially dc-free square wave signal at an excitation frequency of about 100 Hz or more.

9. The corrosion measurement device of claim 8, wherein the excitation signal is a substantially dc-free square wave signal at an excitation frequency of about 200 Hz.

10. The corrosion measurement device of claim 1, further comprising a synchronous rectifier that alternates a polarity of a sensed signal in concert with an alternating polarity of an excitation signal provided to the electrolyte under control of the processing system;
    wherein the processing system is operative to compute at least one corrosion related value based on signals sensed by the sensing circuitry, and wherein the processing system causes the excitation circuitry to initially provide no excitation signal and causes the synchronous rectifier to begin alternating the polarity of a sensed current signal, samples the sensed current while the synchronous rectifier operates with no excitation signal, computes an offset value based on at least one sensed current signal sample, and stores the offset value for subsequent use as an offset correction in computing the at least one corrosion related value.

11. The corrosion measurement device of claim 10, wherein the excitation signal is a square wave signal.

12. The corrosion measurement device of claim 11, wherein the excitation signal is a substantially dc-free square wave signal at an excitation frequency of about 100 Hz or more.

13. The corrosion measurement device of claim 12, wherein the excitation signal is a substantially dc-free square wave signal at an excitation frequency of about 200 Hz.

14. The corrosion measurement device of claim 10, wherein the excitation signal is a substantially dc-free square wave signal at an excitation frequency of about 100 Hz or more.

15. The corrosion measurement device of claim 14, wherein the excitation signal is a substantially dc-free square wave signal at an excitation frequency of about 200 Hz.

16. The corrosion measurement device of claim 1, wherein the processing system is operative to compute at least one corrosion related value based on signals sensed by the sensing circuitry; and
    wherein the processing system causes the excitation circuitry to initially provide no excitation signal, samples a voltage signal sensed by the sensing circuitry while no excitation signal is applied, stores the sensed voltage value as an offset, and thereafter causes the excitation circuitry to provide sinusoidal excitation voltage signals with the offset to the electrolyte and computes at least one corrosion related value based on harmonics of current signals sensed by the sensing circuitry using harmonic distortion analysis.

17. The corrosion measurement system of claim 16, wherein the sensing circuitry senses a voltage across second and third electrodes while no excitation signal is applied.

18. The corrosion measurement device of claim 16, further comprising a switching system that electrically isolates the first electrode from the excitation circuitry while the processing system samples the voltage signal sensed by the sensing circuitry.

19. The corrosion measurement system of claim 18, wherein the sensing circuitry senses a voltage across second and third electrodes while no excitation signal is applied.

* * * * *